United States Patent
Averina et al.

(10) Patent No.: US 9,526,893 B2
(45) Date of Patent: Dec. 27, 2016

(54) BLOOD VOLUME REDISTRIBUTION THERAPY FOR HEART FAILURE

(71) Applicant: Cardiac Pacemakers, Inc., St. Paul, MN (US)

(72) Inventors: Viktoria A. Averina, Roseville, MN (US); Jason J. Hamann, Blaine, MN (US); Stephen Ruble, Lino Lakes, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 592 days.

(21) Appl. No.: 13/926,061

(22) Filed: Jun. 25, 2013

(65) Prior Publication Data

US 2013/0289649 A1 Oct. 31, 2013

Related U.S. Application Data

(63) Continuation of application No. 12/843,444, filed on Jul. 26, 2010, now Pat. No. 8,483,821.
(Continued)

(51) Int. Cl.
*A61N 1/00* (2006.01)
*A61N 1/36* (2006.01)
(Continued)

(52) U.S. Cl.
CPC .......... *A61N 1/3601* (2013.01); *A61B 5/0537* (2013.01); *A61B 5/0538* (2013.01); *A61B 5/0809* (2013.01);
(Continued)

(58) Field of Classification Search
CPC ............ A61N 1/36514; A61N 1/36217; A61N 1/3601; A61N 1/36053; A61N 1/36521
See application file for complete search history.

(56) References Cited

U.S. PATENT DOCUMENTS

| | | | |
|---|---|---|---|
| 4,773,401 A | 9/1988 | Citak et al. | |
| 5,147,294 A * | 9/1992 | Smith ................. | A61K 31/165 |
| | | | 128/898 |

(Continued)

FOREIGN PATENT DOCUMENTS

| | | |
|---|---|---|
| JP | 2007503278 A | 2/2007 |
| JP | 2010534548 A | 11/2010 |

(Continued)

OTHER PUBLICATIONS

Takala, J. "Determinants of splanchnic blood flow." British journal of anaesthesia 77.1 (1996): 50-58.*
(Continued)

*Primary Examiner* — William Levicky
*Assistant Examiner* — Lindsey G Hankins
(74) *Attorney, Agent, or Firm* — Schwegman Lundberg & Woessner, P.A.

(57) ABSTRACT

A first fluid status indicator of a pulmonary fluid status associated with pulmonary edema and a second fluid status indicator of a non-pulmonary fluid status can be used to provide an alert or to control a therapy for pulmonary edema. Additionally, intermittent cardiac blood volume redistribution therapy can be used to provide cardiac conditioning in heart failure patients.

20 Claims, 7 Drawing Sheets

Related U.S. Application Data

(60) Provisional application No. 61/228,745, filed on Jul. 27, 2009.

(51) Int. Cl.
    *A61B 5/053*         (2006.01)
    *A61B 5/08*          (2006.01)
    *A61B 5/00*          (2006.01)
    *A61N 1/365*        (2006.01)

(52) U.S. Cl.
    CPC ......... *A61B 5/4869* (2013.01); *A61N 1/36521* (2013.01); *A61N 1/36585* (2013.01); *A61B 5/4035* (2013.01); *A61N 1/36114* (2013.01)

(56) References Cited

U.S. PATENT DOCUMENTS

| | | | |
|---|---|---|---|
| 5,284,136 | A | 2/1994 | Hauck et al. |
| 6,678,547 | B2 | 1/2004 | Carlson et al. |
| 7,387,610 | B2 | 6/2008 | Stahmann et al. |
| 7,471,290 | B2 | 12/2008 | Wang |
| 7,566,308 | B2 | 7/2009 | Stahmann |
| 2004/0073128 | A1 | 4/2004 | Hatlestad et al. |
| 2004/0102712 | A1 | 5/2004 | Belalcazar et al. |
| 2004/0220632 | A1 | 11/2004 | Burnes |
| 2005/0065575 | A1 | 3/2005 | Dobak |
| 2005/0143779 | A1* | 6/2005 | Libbus ............... A61N 1/36114 607/9 |
| 2005/0203169 | A1* | 9/2005 | Moskowitz ............ A61K 31/00 514/423 |
| 2005/0288718 | A1* | 12/2005 | Sunagawa .......... A61N 1/36114 607/9 |
| 2006/0041280 | A1 | 2/2006 | Stahmann et al. |
| 2006/0100667 | A1 | 5/2006 | Machado et al. |
| 2006/0111754 | A1 | 5/2006 | Rezai et al. |
| 2007/0156061 | A1 | 7/2007 | Hess |
| 2007/0260285 | A1 | 11/2007 | Libbus et al. |
| 2008/0015659 | A1 | 1/2008 | Zhang et al. |
| 2008/0086185 | A1 | 4/2008 | Amurthur et al. |
| 2008/0108907 | A1 | 5/2008 | Stahmann et al. |
| 2009/0018599 | A1 | 1/2009 | Hastings et al. |
| 2009/0036777 | A1* | 2/2009 | Zhang .................. A61B 5/0031 600/459 |
| 2009/0069708 | A1 | 3/2009 | Hatlestad et al. |
| 2010/0004714 | A1 | 1/2010 | Georgakopoulos et al. |
| 2010/0073170 | A1 | 3/2010 | Siejko et al. |
| 2010/0152608 | A1 | 6/2010 | Hatlestad |
| 2011/0022127 | A1 | 1/2011 | Averina et al. |

FOREIGN PATENT DOCUMENTS

| | | |
|---|---|---|
| JP | 2013500138 A | 1/2013 |
| WO | WO-2009020571 A1 | 2/2009 |
| WO | WO-2011017049 A1 | 2/2011 |

OTHER PUBLICATIONS

"U.S. Appl. No. 12/843,444, Non Final Office Action mailed Jun. 11, 2012", 11 pgs.
"U.S. Appl. No. 12/843,444, Notice of Allowance mailed Mar. 15, 2013", 5 pgs.
"U.S. Appl. No. 12/843,444, Response filed Nov. 9, 2012 to Non Final Office Action mailed Jun. 11, 2012", 19 pgs.
"U.S. Appl. No. 13/360,339, Preliminary Statement filed Jan. 27, 2012", 2 pgs.
"U.S. Appl. No. 13/360,339, Response filed to Restriction Requirement mailed Jul. 30, 2012", 11 pgs.
"International Application Serial No. PCT/US2010/043228, International Preliminary Report on Patentability mailed Feb. 9, 2012", 13 pgs.
"International Application Serial No. PCT/US2010/043228, International Search Report mailed Jan. 18, 2011", 7 pgs.
"International Application Serial No. PCT/US2010/043228, Invitation to Pay Additional Fees mailed Nov. 8, 2010", 8 pgs.
"International Application Serial No. PCT/US2010/043228, Written Opinion mailed Jan. 18, 2011", 12 pgs.
"Japanese Application Serial No. 2012-522934, Office Action mailed May 14, 2013", With English Translation, 9 pgs.
Balmain, Sean, et al., "Differences in arterial compliance, microvascular function and venous capacitance between patients with heart failure and either preserved or reduced left ventricular systolic function", Eur J Heart Fail., (9), (Jun. 2007), 865-871.
Burkhoff, D., et al., "Why does pulmonary venous pressure rise after onset of LV dysfunction: a theoretical analysis", Am J Physiol Heart Circ Physiol, 265, (Nov. 1993), H1819-H1828.
Butler, J., et al., "Relationship between heart failure treatment and development of worsening renal function among hospitalized patients", Am Heart J., 147(2), (Feb. 2004), 331-8.
Cotter, G., et al., "Acute heart failure: a novel approach to its pathogenesis and treatment.", Eur J Heart Fail., 4(3), (Jun. 2002), 227-34.
Cotter, G., et al., "Fluid overload in acute heart failure—re-distribution and other mechanisms beyond fluid accumulation.", Eur J Heart Fail., 10(2), (Feb. 2008), 165-9.
Cotter, G., et al., "Increased toxicity of high-dose furosemide versus low-dose dopamine in the treatment of refractory congestive heart failure.", Clin Pharmacol Ther., 62(2), (Aug. 1997), 187-93.
Cotter, G., et al., "The pathophysiology of acute heart failure—Is it all about fluid accumulation?", Am Heart J.,155(1), (Jan. 2008), 9-18.
Duprez, D., et al., "The influence of transdermal glyceryl trinitrate on peripheral circulation in healthy subjects and in patients with congestive cardiac failure.", Eur J Clin Pharmacol., 33(1), (1987), 73-5.
Feigenbaum, M. S., et al., "Contracted Plasma and Blood Volume in Chronic Heart Failure", J Am Coll Cardiol., 35(1), (Jan. 2000), 51-55.
Guntheroth, W. G, et al., "Liver and spleen as venous reservoirs.", Am J Physiol., 204, (Jan. 1963), 35-41.
Hirakawa, S., et al., "Human pulmonary vascular and venous compliances are reduced before and during left-sided heart failure.", J Appl Physiol., 78(1), (Jan. 1995), 323-33.
Jackson, L. B., et al., Digital Filters and Signal Processing, (Second Edition), Kluwer Academic Publishers, Bostonl, MA, (1989), 332-340.
Katz, A. M, et al., "The "modern" view of heart failure: how did we get here?", Circ Heart Fail., 1(1), (May 2008), 63-71.
Krack, A., et al., "The importance of the gastrointestinal system in the pathogenesis of heart failure.", Eur Heart J., 26(22), (Nov. 2005), 2368-74.
Leier, C. V, "Regional blood flow responses to vasodilators and inotropes in congestive heart failure.", Am J Cardiol., 62(8), (Sep. 9, 1988), 86E-93E.
Lindsey, A. W, et al., "Pulmonary blood volume of the dog and its changes in acute heart failure.", Am J Physiol., 190(1), (Jul. 1957), 45-8.
Metra, M., et al., "The pathophysiology of acute heart failure—it is a lot about fluid accumulation.", Am Heart J., 155(1), (Jan. 2008), 1-5.
Miyata, M., et al., "Beneficial effects of Waon therapy on patients with chronic heart failure: Results of a prospective multicenter study", J Cardiol., 52(2), (Oct. 2008), 79-85.
Nieminen, M. S, et al., "Executive summary of the guidelines on the diagnosis and treatment of acute heart failure: the Task Force on Acute Heart Failure of the European Society of Cardiology.", Eur Heart J., 26(4), (Feb. 2005), 384-416.
Nishikimi, T., et al., "The role of natriuretic peptides in cardioprotection", Cardiovasc Res., 69(2), (Feb. 1, 2006), 318-28.
Parameswaran, N, et al., "Increased splenic capacity in response to transdermal application of nitroglycerine in the dog", J Vet Intern Med., 13(1), (Jan.-Feb. 1999), 44-6.
Schneider, A., et al., "The immediate effect of nitroglycerin on total body blood volume distribution in patients with congestive heart failure: a non-invasive study.", Eur Heart J., 8(10), (Oct. 1987), 1119-25.

(56) References Cited

OTHER PUBLICATIONS

Schreiner, B. F, et al., "Pulmonary Blood Volime in Congestive Heart Failure", Circulation, 34, (1966), 249-259.

Sjostrand, T., "Volume and distribution of blood and their significance in regulating the circulation", Physiol Rev., 33(2), (Apr. 1953), 202-28.

Tkachenko, B. I, et al., "A correlation of responses of the resistance and capacitance vessels of the intestine and kidney to changes of impulse in postganglionic nerves under pressor reflexes.", Experientia, 34(10), (Oct. 15, 1978), 1298-9.

Tkachenko, B. I, et al., "Neurogenic responses of resistance and capacitance vessels.", Experientia, 27(7), (Jul. 1971), 782-4.

Tkachenko, B. I, et al., "Relation of efferent impulse activity in splenic nerve to reflexly induced reactions of resistance and capacitance vessels to spleen.", Experientia, 32(8), (Aug. 15, 1976), 1012-4.

Tkachenko, B. I, et al., "Relation of the character of capacitance vessel responses in spleen and small intestine elicited by electrical stimulation of the sympathetic fibres to the level of oxygen exchange in the organs.", Experientia, 32(9), (Sep. 15, 1976), 1168-70.

Tkachenko, B. I, et al., "Responses of resistance and capacitance vessels at various frequency electrical stimulation of sympathetic nerves", Experientia, 25(1), (Jan. 15, 1969), 38-40.

Vanagt, W. Y., et al., "Pacing-induced dys-synchrony preconditions rabbit myocardium against ischemia/reperfusion injury.", Circulation, 114(1 Suppl), Jul. 4, 2006), I264-I269.

Wang, S., et al., "Splanchnic venous pressure-volume relation during experimental acute ischemic heart failure. Differential effects of hydralazine, enalaprilat, and nitroglycerin.", Circulation, ;91(4), (Feb. 15, 1995), 1205-12.

Yancy, C. W, "Vasodilator therapy for decompensated heart failure", J Am Coll Cardiol., 52(3), (Jul. 2008), 208-10.

\* cited by examiner

BLOOD VOLUME REDISTRIBUTION THERAPY FOR HEART FAILURE

CLAIM OF PRIORITY

This application is a continuation of U.S. application Ser. No. 12/843,444, filed Jul. 26, 2010, now issued as U.S. Pat. No. 8,483,821, which claims the benefit of U.S. Provisional Application No. 61/228,745, filed on Jul. 27, 2009, under 35 U.S.C. §119(e), each of which is incorporated herein by reference in its entirety.

BACKGROUND

Heart failure (HF) is a debilitating disease in which abnormal function of the heart leads to inadequately low perfusion of tissues and organs of the body. In the early stages of HF many compensatory mechanisms are employed to maintain proper perfusion of tissues and alleviate stress on the heart. Some examples of such mechanisms include activation of the renin-angiotensin-aldosterone system (RAAS) and blood volume redistribution via neural control. As HF progresses, not only can cardiac function worsen, but the compensatory mechanisms themselves can eventually become maladaptive and start contributing to the symptoms of HF. For example, overactivation of RAAS can lead to severe remodeling of the ventricles. A particularly severe form of heart failure is congestive heart failure (CHF), in which weak pumping of the heart, together with over-active compensatory mechanisms such as sympathetic outflow, can lead to build-up of fluids in the lungs.

Pulmonary edema is a swelling and/or fluid accumulation in the lungs. It represents one of the congestive symptoms of CHF. The poor cardiac function leads to impaired outflow from the lungs, which increases blood pressure in the lungs, especially if systemic organs are constricting and redistributing additional blood from the systemic to the pulmonary loop. The increased pressure within pulmonary circulation can cause leaking of the fluid into lung tissue and air sacs. This can lead to severe respiratory problems, such as shortness of breath. Shortness of breath is the number one symptom with which decompensated CHF patients present to the hospital (~89%).

Current mainstream treatment of pulmonary edema is aimed at reducing total blood volume by administering a diuretic treatment, based on a belief that it is total volume overload which leads to worsening of HF symptoms. However, in many cases total volume overload might not be the cause of decompensation, and, therefore, diuretics may no longer be the optimal treatment and may even cause additional damage, such as worsening renal function.

Overview

This document describes, among other things, a first fluid status indicator of a pulmonary fluid status associated with pulmonary edema and a second fluid status indicator of a non-pulmonary fluid status that can be used to provide an alert or to control a therapy for pulmonary edema. In addition, cardiac conditioning therapy for heart failure patients is described. The conditioning therapy includes cardiac blood volume redistribution.

Example 1 describes an implantable medical device. In this example, the device comprises a first fluid status monitoring circuit configured to monitor a first fluid status indicator of a pulmonary fluid status associated with pulmonary edema, wherein an increase in the first fluid status indicator correlates to an increase in pulmonary fluid associated with pulmonary edema; a second fluid status monitoring circuit configured to monitor a separate and different second fluid status indicator of a non-pulmonary fluid status, wherein an increase in the second fluid status indicator correlates to an increase in the non-pulmonary fluid; a controller, coupled to the first and second fluid status monitoring circuits, the controller configured to use information about the first and second fluid status indicators to determine a therapy control signal to control a therapy; and a therapy circuit, coupled to the controller to receive the therapy control signal, configured to provide therapy, in response to the therapy control signal, to adjust at least one of the pulmonary fluid status or the non-pulmonary fluid status.

In Example 2, the device of Example 1 optionally comprises the second fluid status monitoring circuit configured to monitor a splanchnic impedance measurement representative of fluid status associated with a splanchnic organ.

In Example 3, the device of one or more of Examples 1-2 optionally comprises the second fluid status monitoring circuit configured to monitor at least one of arterial blood pressure, splanchnic impedance, skeletal muscle impedance, or skin impedance.

In Example 4, the device of one or more of Examples 1-3 optionally comprises the controller configured to trigger providing the therapy in response to at least one of a decrease in the second fluid status indicator below a specified threshold value, an increase in the first fluid status indicator above a specified threshold value, a heart failure decompensation alert provided by the medical device, a patient-initiated alert, or a user input.

In Example 5, the device of one or more of Examples 1-4 optionally comprises a neuromodulation circuit configured to provide a neuromodulation therapy to adjust the non-pulmonary fluid status, wherein the neuromodulation therapy includes stimulation or inhibition of at least one of a sympathetic nervous system or a parasympathetic nervous system.

In Example 6, the device of one or more of Examples 1-5 optionally comprises the therapy circuit configured to provide at least one of a localized vasodilation therapy or a localized vasoconstriction therapy, wherein the at least one of a localized vasodilation therapy or a localized vasoconstriction therapy includes at least one of a neuromodulation therapy, a drug therapy, or a vessel blood flow control therapy.

In Example 7, the device of one or more of Examples 1-6 optionally comprises the therapy circuit configured to concurrently deliver at least one of a localized vasodilation therapy or a localized vasoconstriction therapy to at least two separate localized vascular regions to adjust a balance between fluid status in the two separate localized regions.

In Example 8, the device of one or more of Examples 1-7 optionally comprises the controller configured to decrease or stop therapy in response to at least one of: an increase in the first fluid status indicator above a first specified threshold value; a decrease in the first fluid status indicator below a second specified threshold value; an increase in the second fluid status indicator above a third specified threshold value; or a decrease in the second fluid status indicator below a fourth specified threshold value.

In Example 9, the device of one or more of Examples 1-8 optionally comprises the controller configured to use information about the first and second fluid status indicators to stop therapy after a specified period of time.

In Example 10, the device of one or more of Examples 1-9 optionally comprises a heart signal detection circuit configured to detect a heart signal of a subject, wherein the controller is coupled to the heart signal detection circuit and configured to trigger providing the therapy synchronized with a specified portion of the subject's cardiac cycle.

In Example 11, the device of one or more of Examples 1-10 optionally comprises a posture sensing circuit configured to detect a posture of a subject, wherein the controller is configured to use (1) information about the first and second fluid status indicators, and (2) information about the posture of the subject to determine the therapy control signal to control the therapy.

In Example 12, the device of one or more of Examples 1-11 optionally comprises an activity sensing circuit configured to detect a physical activity level of a subject, wherein the controller is configured to use (1) information about the first and second fluid status indicators, and (2) information about the activity level of the subject to determine the therapy control signal to control the therapy.

Example 13 describes a method. In this example, the method comprises monitoring a first fluid status indicator of a pulmonary fluid status associated with pulmonary edema; monitoring a separate and different second fluid status indicator of a non-pulmonary fluid status; and using information about the first and second fluid status indicators, controlling a therapy to adjust at least one of the pulmonary fluid status or the non-pulmonary fluid status.

In Example 14, the method of Example 13 optionally comprises monitoring a splanchnic impedance measurement representative of fluid status associated with a splanchnic organ.

In Example 15, the method of one or more of Examples 13-14 optionally comprises measuring a first impedance vector across both a pulmonary region and a splanchnic region of interest; measuring a second impedance vector across a pulmonary region but not across the splanchnic region of interest; and subtracting the second impedance vector from the first impedance vector to determine the splanchnic impedance.

In Example 16, the method of one or more of Examples 13-15 optionally comprises monitoring at least one of arterial blood pressure, splanchnic impedance, skeletal muscle impedance, or skin impedance.

In Example 17, the method of one or more of Examples 13-16 optionally comprises triggering providing the therapy by a decrease in the second fluid status indicator below a specified threshold value.

In Example 18, the method of one or more of Examples 13-17 optionally comprises controlling a neuromodulation to stimulate or inhibit at least one of a sympathetic nervous system or a parasympathetic nervous system in a region associated with the non-pulmonary fluid.

In Example 19, the method of one or more of Examples 13-18 optionally comprises controlling at least one of vasodilation or vasoconstriction in a localized vascular region of a subject by providing at least one of a neuromodulation therapy, a drug therapy, or a vessel blood flow control therapy.

In Example 20, the method of one or more of Examples 13-19 optionally comprises concurrently controlling at least one of vasodilation or vasoconstriction in at least two separate localized vascular regions to adjust a balance between fluid status in the two separate localized regions.

In Example 21, the method of one or more of Examples 13-20 optionally comprises decreasing or stopping therapy in response to at least one of: an increase in the first fluid status indicator above a first specified threshold value; a decrease in the first fluid status indicator below a second specified threshold value; an increase in the second fluid status indicator above a third specified threshold value; or a decrease in the second fluid status indicator below a fourth specified threshold value.

In Example 22, the method of one or more of Examples 13-21 optionally comprises using information about the first and second fluid status indicators to stop therapy after a specified period of time.

In Example 23, the method of one or more of Examples 13-22 optionally comprises synchronizing delivery of the therapy with a specified portion of the subject's cardiac cycle.

In Example 24, the method of one or more of Examples 13-23 optionally comprises detecting a patient posture, wherein the controlling the therapy comprises using (1)information about the first and second fluid status indicators, and (2) information about the patient posture to adjust at least one of the pulmonary fluid status or the non-pulmonary fluid status.

In Example 25, the method of one or more of Examples 13-24 optionally comprises detecting a patient physical activity level, wherein the controlling the therapy comprises using (1) information about the first and second fluid status indicators, and (2) information about the patient physical activity level to adjust at least one of the pulmonary fluid status or the non-pulmonary fluid status.

Example 1A describes an apparatus. In this example, the apparatus comprises a neuromodulator circuit, configured to deliver neuromodulation to a splanchnic region; and a controller circuit, coupled to the neuromodulator circuit, the controller circuit configured to control the neuromodulator circuit to deliver the neuromodulation to the splanchnic region during a specified period of time in an amount sufficient to modulate cardiac blood volume during at least a portion of the specified period of time.

In Example 2A, the apparatus of Example 1A optionally comprises a cardiac blood volume status monitoring circuit providing a cardiac blood volume status indicator to the controller circuit to control the neuromodulator circuit to deliver the neuromodulation to the splanchnic region.

In Example 3A, the apparatus Example 2A optionally comprises a splanchnic blood volume status monitoring circuit providing a splanchnic blood volume status indicator to the controller circuit to control the neuromodulator circuit to deliver the neuromodulation to the splanchnic region.

In Example 4A, the apparatus of one or more of Examples 2A-3A optionally comprises an intracardiac impedance measurement monitoring circuit providing an intracardiac impedance based indicator of cardiac blood volume status to the controller circuit to control the neuromodulator circuit to deliver the neuromodulation to the splanchnic region.

In Example 5A, the apparatus of Example 4A optionally comprises the intracardiac impedance measurement monitoring circuit configured to provide a stroke impedance based indicator of cardiac blood volume status to the controller circuit to control the neuromodulator circuit to deliver the neuromodulation to the splanchnic region.

In Example 6A, the apparatus of one or more of Examples 2A-5A optionally comprises a comparator circuit configured to compare the cardiac blood volume status indicator to a threshold, wherein the controller is configured to adjust an amount of neuromodulation to the splanchnic region when the cardiac blood volume status indicator is below a first value of the threshold.

In Example 7A, the apparatus of Example 6A optionally comprises the controller configured to increase an amount of sympathetic nerve stimulation to the splanchnic region when the cardiac blood volume status indicator is below a first value of the threshold.

In Example 8A, the apparatus of one of more of Examples 6A-7A optionally comprises the controller configured to decrease an amount of sympathetic nerve inhibition to the splanchnic region when the cardiac blood volume status indicator is below a first value of the threshold.

In Example 9A, the apparatus of one or more of Examples 6A-8A optionally comprises the controller configured to decrease an amount of parasympathetic nerve stimulation to the splanchnic region when the cardiac blood volume status indicator is below a first value of the threshold.

In Example 10A, the apparatus of one or more of Examples 6A-9A optionally comprises the controller configured to increase an amount of parasympathetic nerve inhibition to the splanchnic region when the cardiac blood volume status indicator is below a first value of the threshold.

In Example 11A, the apparatus of Example 6A optionally comprises the controller configured to adjust an amount of neuromodulation to the splanchnic region when the cardiac blood volume status indicator is above a second value of the threshold.

In Example 12A, the apparatus of Example 11A optionally comprises the controller configured to decrease an amount of sympathetic nerve stimulation to the splanchnic region when the cardiac blood volume status indicator is above a second value of the threshold.

In Example 13A, the apparatus of one or more of Examples 11A-12A optionally comprises the controller configured to increase an amount of sympathetic nerve inhibition to the splanchnic region when the cardiac blood volume status indicator is above a second value of the threshold.

In Example 14A, the apparatus of one or more of Examples 11A-13A optionally comprises the controller configured to increase an amount of parasympathetic nerve stimulation to the splanchnic region when the cardiac blood volume status indicator is above a second value of the threshold.

In Example 15A, the apparatus of one or more of Examples 11A-14A optionally comprises the controller configured to decrease an amount of parasympathetic nerve inhibition to the splanchnic region when the cardiac blood volume status indicator is above a second value of the threshold.

In Example 16A, the apparatus of one or more of Examples 2A-15A optionally comprises the cardiac blood volume status monitoring circuit including a transthoracic impedance measurement monitoring circuit providing a pulmonary impedance based indicator of cardiac blood volume status to the controller circuit to control the neuromodulator circuit to deliver the neuromodulation to the splanchnic region; wherein the controller is configured to adjust an amount of neuromodulation to the splanchnic region in response to a decrease in transthoracic impedance.

In Example 17A, the apparatus of Example 16A optionally comprises the controller configured to do at least one of: decrease an amount of sympathetic nerve stimulation to the splanchnic region; increase an amount of sympathetic nerve inhibition to the splanchnic region; increase an amount of parasympathetic nerve stimulation to the splanchnic region; or decrease an amount of parasympathetic nerve inhibition to the splanchnic region.

In Example 18A, the apparatus of one or more of Examples 1A-17A optionally comprises the neuromodulator circuit configured to provide localized splanchnic vasoconstriction therapy to increase cardiac blood volume.

In Example 19A, the apparatus of one or more of Examples 1A-18A optionally comprises the neuromodulator circuit configured to provide localized splanchnic vasodilation therapy to decrease cardiac blood volume.

In Example 20A, the apparatus of one or more of Examples 1A-19A optionally comprises at least one of: a heart rate monitoring circuit; a cardiac stroke volume monitoring circuit; a cardiac contractility monitoring circuit; an arterial blood pressure monitoring circuit; or a venous blood pressure monitoring circuit; wherein the controller is configured to adjust an amount of neuromodulation to the splanchnic region in response to at least one of: an increase in the heart rate above a first specified threshold value; a decrease in the cardiac stroke volume below a second specified threshold value; a decrease in the measurement of cardiac contractility below a third specified threshold value; a decrease in arterial blood pressure below a fourth specified threshold value; or an increase in venous blood pressure above a fifth specified threshold value.

In Example 21A, the apparatus of Example 20A optionally comprises the controller is configured to do at least one of: decrease an amount of sympathetic nerve stimulation to the splanchnic region; increase an amount of sympathetic nerve inhibition to the splanchnic region; increase an amount of parasympathetic nerve stimulation to the splanchnic region; or decrease an amount of parasympathetic nerve inhibition to the splanchnic region.

In Example 22A, the apparatus of one or more of Examples 1A-21A optionally comprises a pacing circuit, coupled to the controller; wherein the controller is configured to control the pacing circuit to issue pacing pulses that are unsynchronized to an intrinsic contraction or offset enough from the intrinsic contraction to provide a stretch a portion of a heart chamber.

In Example 23A, the apparatus of one or more of Examples 1A-22A optionally comprises an atrial proarrhythmia condition sensor, wherein the controller is configured control delivery of neuromodulation to the splanchnic region in response to detection of an atrial proarrhythmia condition.

In Example 24A, the apparatus of Example 23A optionally comprises the neuromodulator circuit configured to deliver neuromodulation to the splanchnic region in association with an anti-tachyarrhythmia therapy, including defibrillation or anti-tachyarrhythmia pacing; wherein the neuromodulation includes at least one of: increasing an amount of parasympathetic nerve stimulation, decreasing an amount of parasympathetic nerve inhibition, increasing and amount of sympathetic nerve inhibition, or decreasing an amount of sympathetic nerve stimulation.

Example 25A describes a method. In this example, the method comprises delivering neuromodulation to a splanchnic region; and controlling delivery of the neuromodulation to the splanchnic region during a specified period of time in an amount sufficient to modulate cardiac blood volume during at least a portion of the specified period of time.

In Example 26A, the method of Example 25A optionally comprises monitoring a cardiac blood volume status; providing a cardiac blood volume status indicator using the monitored cardiac blood volume status; and controlling delivery of the neuromodulation to the splanchnic region using the cardiac blood volume status indicator.

In Example 27A, the method of Example 26A optionally comprises monitoring a splanchnic blood volume status; providing a splanchnic blood volume status indicator using the monitored splanchnic blood volume status; and controlling delivery of the neuromodulation to the splanchnic region using the splanchnic blood volume status indicator.

In Example 28A, the method of one or more of Examples 26A-27A optionally comprises monitoring an intracardiac impedance, providing an intracardiac impedance based indicator of cardiac blood volume status using the monitored intracardiac impedance, and controlling delivery of the neuromodulation to the splanchnic region using the intracardiac impedance based indicator of cardiac blood volume status.

In Example 29A, the method of Example 28A optionally comprises providing a stroke impedance based indicator of cardiac blood volume.

In Example 30A, the method of one or more of Examples 26A-29A optionally comprises comparing the cardiac blood volume status indicator to a threshold; and adjusting an amount of neuromodulation to the splanchnic region when the cardiac blood volume status indicator is below a first value of the threshold.

In Example 31A, the method of Example 30A optionally comprises increasing an amount of sympathetic nerve stimulation to the splanchnic region when the cardiac blood volume status indicator is below a first value of the threshold.

In Example 32A, the method of one or more of Examples 30A-31A optionally comprises decreasing an amount of sympathetic nerve inhibition to the splanchnic region when the cardiac blood volume status indicator is below a first value of the threshold.

In Example 33A, the method of one or more of Examples 30A-32A optionally comprises decreasing an amount of parasympathetic nerve stimulation to the splanchnic region when the cardiac blood volume status indicator is below a first value of the threshold.

In Example 34A, the method of one or more of Examples 30A-33A optionally comprises increasing an amount of parasympathetic nerve inhibition to the splanchnic region when the cardiac blood volume status indicator is below a first value of the threshold.

In Example 35A, the method of Example 30A optionally comprises adjusting an amount of neuromodulation to the splanchnic region when the cardiac blood volume status indicator is above a second value of the threshold.

In Example 36A, the method of Example 35A optionally comprises decreasing an amount of sympathetic nerve stimulation to the splanchnic region when the cardiac blood volume status indicator is above a second value of the threshold.

In Example 37A, the method of one or more of Examples 35A-36A optionally comprises increasing an amount of sympathetic nerve inhibition to the splanchnic region when the cardiac blood volume status indicator is above a second value of the threshold.

In Example 38A, the method of one or more of Examples 35A-37A optionally comprises increasing an amount of parasympathetic nerve stimulation to the splanchnic region when the cardiac blood volume status indicator is above a second value of the threshold.

In Example 39A, the method of one or more of Examples 35A-38A optionally comprises decreasing an amount of parasympathetic nerve inhibition to the splanchnic region when the cardiac blood volume status indicator is above a second value of the threshold.

In Example 40A, the method of one or more of Examples 26A-39A optionally comprises monitoring a transthoracic impedance measurement; using the transthoracic impedance measurement to provide a pulmonary impedance based indication of cardiac blood volume status; and adjusting an amount of neuromodulation delivered to the splanchnic region in response to a decrease in transthoracic impedance.

In Example 41A, the method of Example 40A optionally comprises at least one of: decreasing an amount of sympathetic nerve stimulation to the splanchnic region; increasing an amount of sympathetic nerve inhibition to the splanchnic region; increasing an amount of parasympathetic nerve stimulation to the splanchnic region; or decreasing an amount of parasympathetic nerve inhibition to the splanchnic region.

In Example 42A, the method of one or more of Examples 25A-41A optionally comprises providing localized splanchnic vasoconstriction therapy to increase cardiac blood volume.

In Example 43A, the method of one or more of Examples 25A-42A optionally comprises providing localized splanchnic vasodilation therapy to decrease cardiac blood volume.

In Example 44A, the method of one or more of Examples 25A-43A optionally comprises monitoring at least one of a heart rate, a cardiac stroke volume, a cardiac contractility, an arterial blood pressure, or a venous blood pressure; and adjusting an amount of neuromodulation to the splanchnic region in response to at least one of an increase in the heart rate above a first specified threshold value, a decrease in the cardiac stroke volume below a second specified threshold value, a decrease in the measurement of cardiac contractility below a third specified threshold value, a decrease in arterial blood pressure below a fourth specified threshold value, or an increase in venous blood pressure above a fifth specified threshold value.

In Example 45A, the method of Example 44A optionally comprises decreasing an amount of sympathetic nerve stimulation to the splanchnic region;

increasing an amount of sympathetic nerve inhibition to the splanchnic region; increasing an amount of parasympathetic nerve stimulation to the splanchnic region; or decreasing an amount of parasympathetic nerve inhibition to the splanchnic region. In Example 46A, the method of one or more of Examples 25A-45A optionally comprises delivering cardiac pacing pulses that are unsynchronized to an intrinsic contraction or offset enough from the intrinsic contraction to provide a stretch to a portion of a heart chamber.

In Example 47A, the method of one or more of Examples 25A-46A optionally comprises detecting an atrial proarrhythmia condition; and delivering neuromodulation to the splanchnic region in response to detection of an atrial proarrhythmia condition.

In Example 48A, the method of Example 47A optionally comprises delivering neuromodulation to the splanchnic region in association with an anti-tachyarrhythmia therapy, including defibrillation or anti-tachyarrhythmia pacing; wherein the neuromodulation includes at least one of: increasing an amount of parasympathetic nerve stimulation, decreasing an amount of parasympathetic nerve inhibition, increasing and amount of sympathetic nerve inhibition, or decreasing an amount of sympathetic nerve stimulation.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that pulmonary edema in HF patients can be alleviated by controllably redistributing excessive pulmonary blood volume into one or more targeted high fluid-capacitance systemic vascular beds, such as those in the splanchnic organs, skeletal muscle, or skin. It is believed that the mechanism leading to pulmonary edema in HF patients is fluid redistribution toward the lungs, rather than an increase in total blood volume.

Redistribution of excessive pulmonary blood volume away from the lungs can be achieved, for example, by targeted localized vasodilation of systemic arterioles, or a targeted localized increase in venous capacitance or increase in venous resistance.

Figure 1:
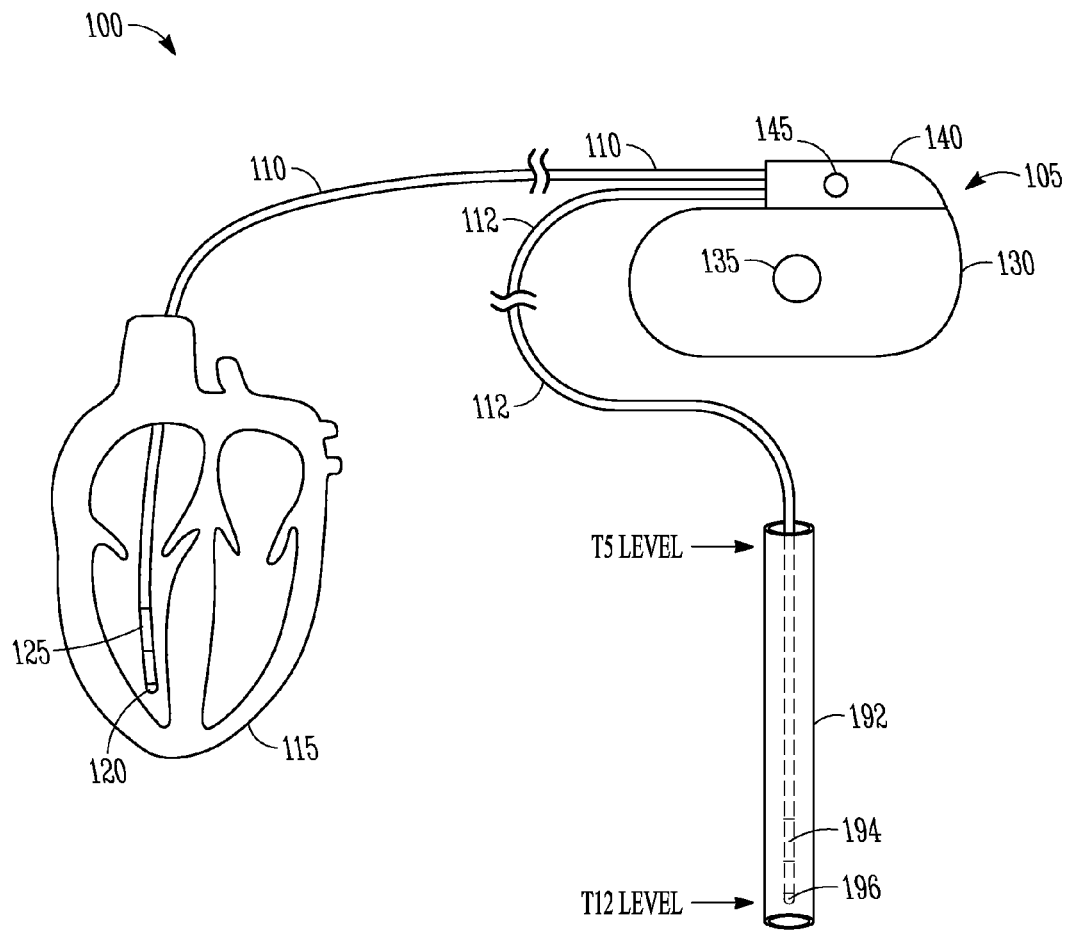
FIG. 1 is an illustration of an example of a medical device including a cardiac function management device with leadwires going to the heart and splanchnic organs.

FIG. 1 illustrates an example of a cardiac function management system 100. In this example, the system 100 can include, among other things, a cardiac function management device ("CFM") 105 and a leadwire ("lead") 110 for communicating signals between the device 105 and a portion of a living organism, such as a heart 115. Examples of the device 105 can include bradycardia and antitachycardia pacemakers, cardioverters, defibrillators, combination pacemaker/defibrillators, cardiac resynchronization devices, neuromodulation devices, drug delivery devices, or any other cardiac rhythm management apparatus capable of monitoring cardiovascular function or providing cardiovascular therapy such as for benefit of the heart 115. The system 100 can include other components such as, for example, a local or remote programmer capable of communicating with the device 105, or additional satellite devices such as a pulmonary artery pressure sensor.

The system 100 can include a second lead 112 for communicating signals between the device 105 and a blood or lymphatic vessel 192 associated with a splanchnic organ.

The splanchnic organs can generally be understood as visceral abdominal organs, including one or more of the spleen, liver, pancreas, stomach, gallbladder, small intestines, and large intestines. Splanchnic organs are generally located between the fifth and twelfth thoracic rib levels ("T5" through "T12"), which can also be referred to as the "splanchnic region."

In an example, the system 100 can be implantable or partially implantable in a living organism, such as in a pectoral or abdominal region of a human patient, or elsewhere. In an example, one or more portions of the system 100 (e.g., device 105) can be disposed external to the human patient. In the illustrated example, portions of the lead 110 are disposed in the right ventricle; however, any other positioning of lead 110 can be used. For example, the lead 110 can be positioned in the atrium or elsewhere. In the illustrated example, portions of the lead 112 are disposed in a blood or lymphatic vessel 192 associated with a splanchnic organ; however, any other positioning of lead 112 within 3the splanchnic region or other regions can be used. In an example, the leads 110 and 112 can include commercially available unipolar or bipolar pacing leads. The system 100 can include one or more other leads or electrodes (e.g., with a lead, or leadless), such as in addition or alternative to leads 110 and 112, appropriately disposed, such as in or around the heart 115, the splanchnic region, or elsewhere. An example of leadless electrostimulation electrodes is described in Hastings et al. U.S. Patent Publication No. 2009/0018599 entitled "CARDIAC STIMULATION USING LEADLESS ELECTRODE ASSEMBLIES," the disclosure of which is incorporated herein by reference in its entirety.

In an example, the system 100 can include at least four electrodes such as for sensing a thoracic or splanchnic impedance indicative of fluid status. An example of impedance sensing using four electrodes is described in Hauck et al. U.S. Pat. No. 5,284,136 entitled "DUAL INDIFFERENT ELECTRODE PACEMAKER," assigned to the assignee of the present patent application, the disclosure of which is incorporated herein by reference in its entirety, including its description of an impedance sensing system. The present systems and methods can include using a different number of electrodes (e.g., 2 or 3 electrodes, or more than 4 electrodes). In an example, a first conductor of the multiconductor lead 110 can electrically couple a first electrode, such as a tip electrode 120 (e.g., disposed at the apex of the right ventricle of the heart 115), to the device 105. A second conductor of the multiconductor lead 110 can independently electrically couple a second electrode, such as a ring electrode 125, to the device 105. In an example, a first conductor of the multiconductor lead 112 can electrically couple a first electrode, such as a tip electrode 196 (e.g., disposed in the splanchnic region above T12), to the device 105. A second conductor of the multiconductor lead 112 can independently electrically couple a second electrode, such as a ring electrode 194 (e.g., disposed in the splanchnic region below T5), to the device 105. In an example, the device 105 can include a hermetically sealed housing 130, formed from a conductive metal, such as titanium. The housing 130 (also referred to as a "case" or "can") can be substantially covered over its entire surface by a suitable insulator, such as silicone rubber, except for at a window that forms a third electrode, referred to as a "case" or a "can" electrode 135. In an example, a header 140 can be mounted on the housing 130 such as for receiving the leads 110 and 112. The header 140 can be formed of an insulative material, such as molded plastic. The header 140 can include at least one receptacle, such as for receiving the leads 110 and 112 and electrically coupling conductors of the leads 110 and 112 to the device 105. The header 140 can include a fourth electrode, which can be referred to as an indifferent electrode 145.

Figure 2:
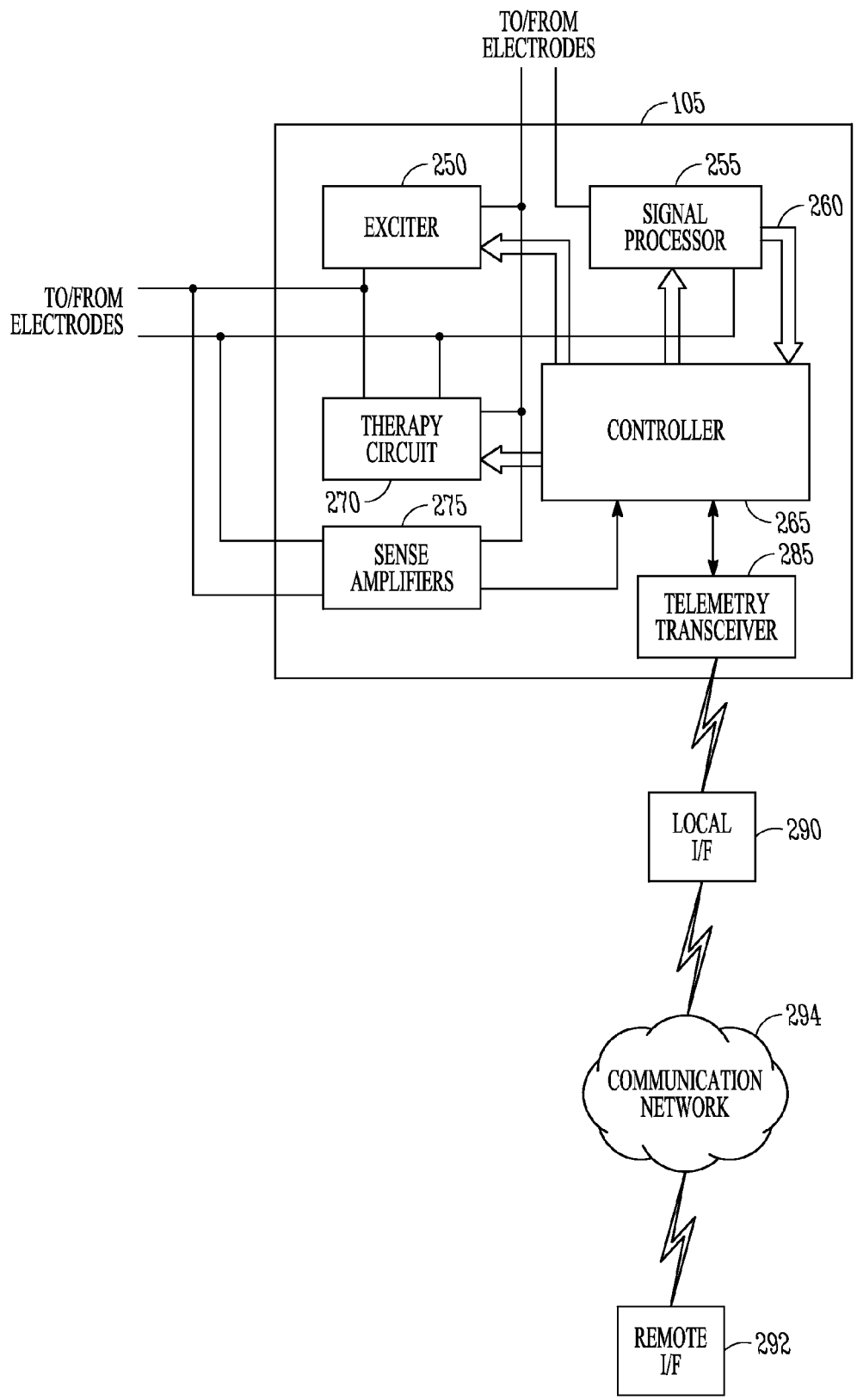
FIG. 2 is a block diagram illustrating an example of portions of the medical device together with schematic illustrations of connections to the various electrodes.

FIG. 2 illustrates generally portions of the device 105, together with schematic illustrations of connections to the various electrodes. The device 105 can include an electrical stimulation source, such as an exciter 250. The exciter 250 can deliver an electrical excitation signal, such as a strobed sequence of current pulses or other measurement stimuli, to the heart 115 (e.g., between the ring electrode 125 and the tip electrode 120, or using any other electrode configuration suitable for delivering the current pulses), and to the splanchnic region (e.g. between the ring electrode 194 and the tip electrode 196, our using any other electrode configuration suitable for delivering the current pulses). The exciter 250 can be configured to receive one or more clock or other control signals from a controller 265. In response to the excitation signal provided by the exciter 250, a response signal can be sensed by signal processor 255 (e.g., between the tip electrode 120 and the indifferent electrode 145, between the tip electrode 196 and the indifferent electrode 145, or any other suitable electrode configuration). In an example, the response signal sensed by the signal processor 255 can be a voltage that represents a transthoracic (e.g., across a portion of the chest or thorax) or a splanchnic (e.g. across a splanchnic organ) impedance.

An example of an approach for measuring transthoracic impedance is described in Stahmann et al. U.S. Pat. No. 7,387,610 entitled "THORACIC IMPEDANCE DETECTION WITH BLOOD RESISTIVITY COMPENSATION," assigned to the assignee of the present application, the disclosure of which is incorporated herein by reference in its entirety, including its description of an approach for measuring impedance, such as for the present applications of measuring transthoracic or splanchnic impedance.

In an example, an impedance-derived fluid status signal can be obtained by measuring transthoracic (across the chest or thorax) impedance or splanchnic (across a splanchnic organ or region) impedance. For example, a transthoracic impedance can be measured to obtain a first fluid status indicator of a pulmonary fluid status associated with pulmonary edema, wherein an increase in the first fluid status indicator correlates to an increase in pulmonary fluid associated with pulmonary edema. The first fluid status indicator can be monitored by a first fluid status monitoring circuit which includes the exciter 250, the signal processor 255, and electrodes 120 and 125, for example. In addition, a splanchnic impedance can be measured to obtain a second fluid status indicator of a splanchnic fluid status, wherein an increase in the second fluid status indicator correlates to an increase in the splanchnic fluid. The second fluid status indicator can be monitored by a second fluid status monitoring circuit which includes the exciter 250, the signal processor 255, and electrodes 194 and 196, for example.

The controller 265 can be configured to use information about the first and second fluid status indicators to control therapy provided by the therapy circuit 270. In an example, the controller 265 can be configured to use other information, in addition to or in place of information about the first and second fluid status indicators, to control therapy provided by the therapy circuit 270. Examples of such information can include a heart failure decompensation alert, a sensed physiologic parameter, a patient-initiated alert, or a user input. The therapy provided by the therapy circuit can adjust at least one of the first or second fluid statuses. Examples of therapies that can be provided by the therapy circuit 270 include neuromodulation therapy, drug therapy, or vessel blood flow control therapy. In the example shown in FIG. 2, the therapy circuit 270 can be included within the cardiac function management device 105. In other examples, the therapy circuit 270 can be part of a separate implanted or external device. If the therapy circuit 270 is part of a separate device, the device 105 can communicate with the therapy circuit. This can include direct communication between two devices in or on the human body, wherein such communication can be carried out within the human body, such as via inductive coupling, ultrasonic communication, or using body tissue as an electrical conductor, as illustrative examples. It can additionally or alternatively include indirect communication between two implanted devices, or between an implanted and an external device, such as by using a local or remote external device as an intermediary for performing the communication. An illustrative example can include communicating between an implanted device 105 and a therapy circuit located in a separately implanted device, such as by using the Boston Scientific Corp. (Cardiac Pacemakers, Inc.) LATITUDE® System, which can automatically collect information from a subject's implanted medical device 105 and communicate the information to a another one of the subject's implanted or ambulatory personal medical device, such as via a local external interface 290 that can be communicatively coupled via a communication network 294 to a secure remote computer 292.

FIG. 2 illustrates an example of sense amplifiers 275, one or more of which can be used to monitor electrical heart activity within the subject, such as for synchronizing therapy delivery with a specified portion of the subject's cardiac cycle, as described below. In addition, FIG. 2 illustrates a telemetry transceiver 285, which can be configured to receive information from the controller 265 (e.g. information about the first and second fluid status indicators, or information about controlling the therapy) and communicate the information, such as through a unidirectional or bidirectional wireless communication link with an external local interface 290. In certain examples, the external local interface 290 can further unidirectionally or bidirectionally communicate with an external remote interface 292, wirelessly or otherwise, such as via a shared communication or computer network 294. The remote interface 292 can be configured to provide an alert or alarm, thereby allowing for home monitoring or remote monitoring of a subject by a physician or other health care provider.

Figure 3:
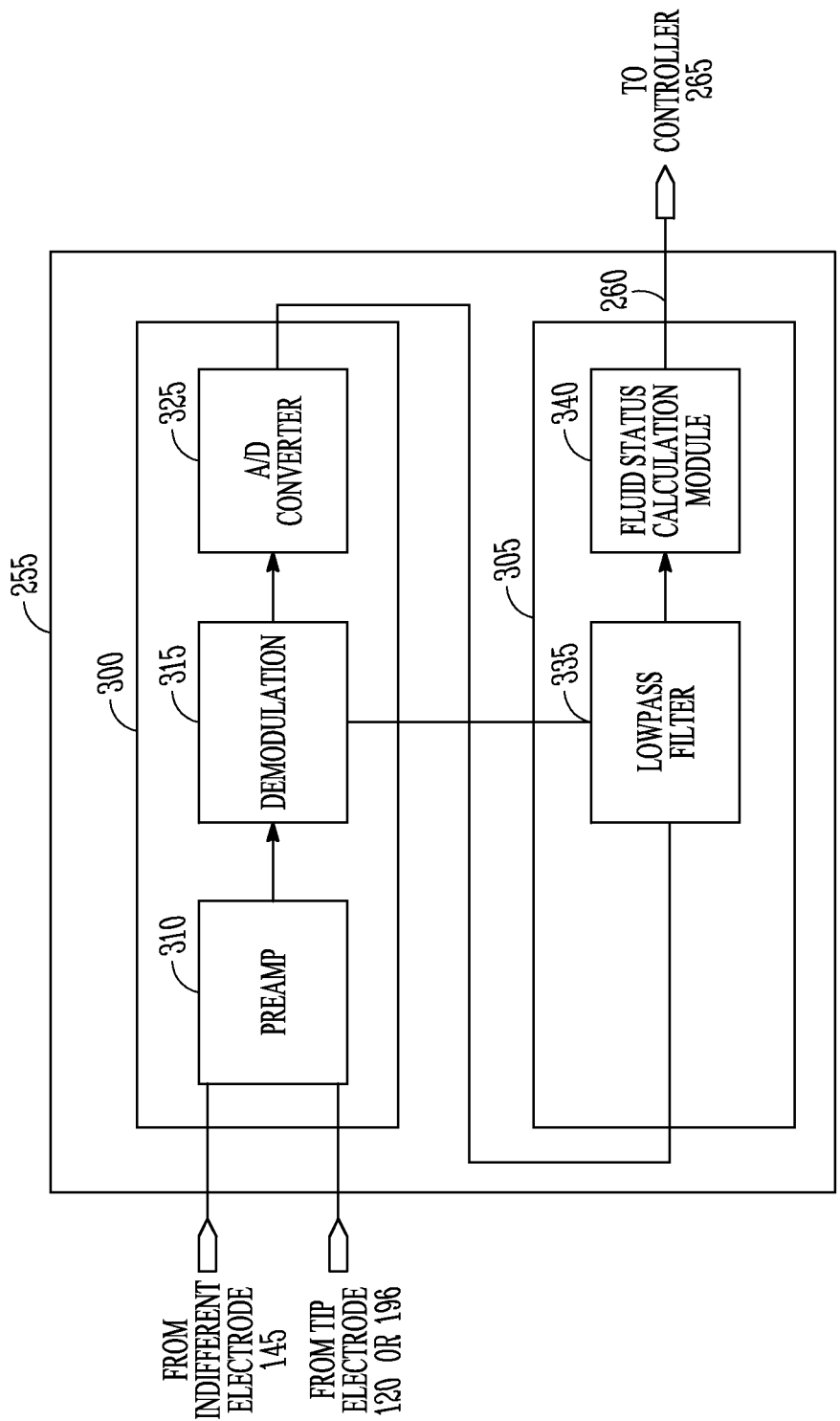
FIG. 3 is a block diagram illustrating generally an example of portions of a signal processor.

FIG. 3 illustrates generally an example of one or more portions of the signal processor 255. The signal processor 255 can include an analog signal processing circuit 300 and a digital signal processing circuit 305. Inputs of a preamplifier 310 (also referred to as a preamp or a receiver) of an analog signal processing circuit 300 can be electrically coupled to the indifferent electrode 145 and the tip electrodes 120 and 196 such as for receiving a signal in response to the above-described stimuli provided by the exciter 250. A time division multiplex scheme can be used by the exciter 250 and the signal processor 255 such that excitation signals are provided to (and responsive measurements are obtained from) the desired vectors (e.g., transthoracic vector and transsplanchnic vector) at non-overlapping times, thereby allowing separate inputs from the pulmonary and splanchnic regions. In another example, separate signal processors 255 can be provided, such as for separately monitoring or processing the pulmonary and splanchnic impedance signals. The analog signal processing circuit 300 can include a demodulator 315, such as receiving the output of the preamplifier 310, and providing an output signal to a lowpass filter 335. The output signal from the lowpass filter 335 can be received by an analog-to-digital (A/D) converter 325.

In an example, the A/D converter 325 can be implemented as a 12-bit, successive approximation type switched-capacitor A/D converter having an input range of approximately 1 Volt. In one example, A/D converter 325 provides one 12-bit word corresponding to a sequence of current pulses delivered by exciter 250. Many different implementations of A/D converter 325 can be suitable for use in the present systems and methods.

In an example, the lowpass filter 335 can include a single-pole infinite impulse response (IIR) digital filter that can receive a 12-bit digital output signal from the A/D converter 325. The lowpass filter 335 can attenuate or remove frequency components above its lowpass cutoff frequency of approximately 0.1 Hz. Many other different examples of the lowpass filter 335 can be suitable for use in the present systems and methods. The lowpass filter 335 can advantageously attenuate frequency components of the signal that exceed the lowpass cutoff frequency of the lowpass filter 335. Attenuated frequencies can include the cardiac stroke signal, resulting from changes in blood volume in heart 115 as it contracts during each cardiac cycle, which appears as a component of the transthoracic impedance signal. In an example, the lowpass cutoff frequency of the filter 335 can be adaptively based on a heart rate of the patient. In an example, the lowpass cutoff frequency can be independent of any breathing rate signal obtained from the patient.

In an example, the lowpass filter 335 can use a Chebyshev filter. In an example, the lowpass filter 335 can include an Elliptic filter. In an example, the lowpass filter 335 can use a state-space structure, rather than a conventional direct form structure. The state-space structure can further reduce the effects of coefficient quantization and round-off noise. An example of such a state-space structure is described in Leland B. Jackson, "Digital Filters and Signal Processing," $2^{nd}$ ed., pp. 332-340, Kluwer Academic Publishers, Boston, Mass., the disclosure of which is incorporated herein by reference.

In an example, a digital signal processing circuit 305 can be included within the controller 265 such as, for example, as a sequence of instructions executed by a microprocessor. In an example, the digital signal processing circuit 305 can include separately implemented hardware portions dedicated to performing the digital signal processing tasks described herein. A fluid status calculation module 340 can receive an output signal from the lowpass filter 335, and can provide a resulting fluid status indicator at node 260 to the controller 265, such as explained below. In an example, an fluid status calculation module 340 can be implemented as a sequence of instructions executed on any suitable microprocessor. In an example, the fluid status calculation module 340 can be implemented as any other hardware or software configuration capable of calculating a fluid status indicator based on impedance-derived fluid status information.

In an example, the fluid status calculation module 340 can include a comparator, such as for comparing the lowpass-filtered pulmonary or splanchnic impedance signals to a respective threshold value. An output of the comparison can be used to provide a respective fluid status indicator, for example, indicating excess fluid in the particular region when its impedance falls below a specified threshold value. In an example, the specified threshold value can be specified using a long-term or other baseline value of the impedance, such as obtained from the subject during a normal condition (e.g., no edema). For example, the specified threshold value can be specified as an offset from such normal condition value. In an example, the specified threshold value can be specified using a value obtained during abnormal conditions, such as during a decompensation episode, or a time period preceding an associated decompensation episode.

In an example, a difference or ratio between a long-term average (or other baseline measure of central tendency) and a short-term average (or other more acute measure of central tendency) can be used as a fluid status indication, or compared to a threshold value or otherwise signal-processed to obtain a resulting fluid status indication.

In an example, a histogram approach can be used to determine fluid status. An example of such a histogram approach is described in Hatlestad et al. U.S. Patent Publication No. 2009/0069708, entitled "HISTOGRAM-BASED THORACIC IMPEDANCE MONITORING," which is incorporated by reference herein in its entirety, including its discussion of using a histogram approach to determine fluid status.

Figure 4A:
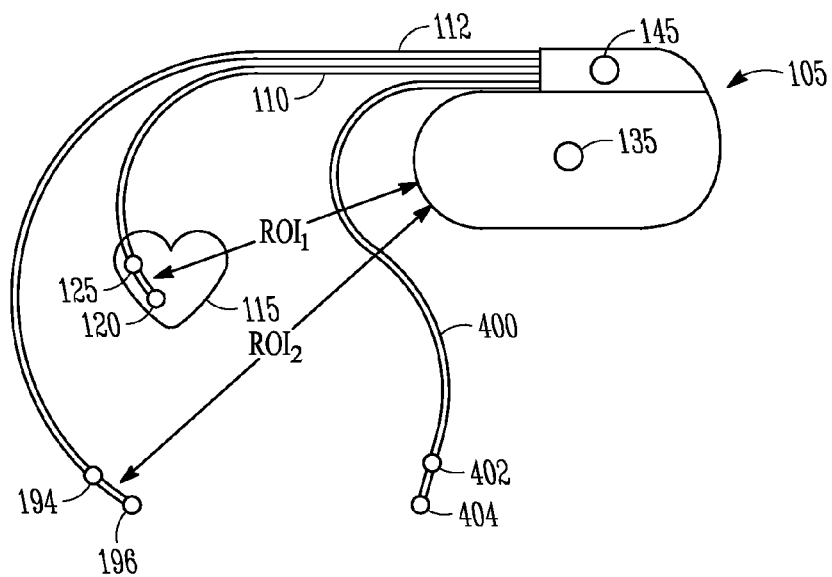
FIGS. 4A-4E are schematic diagrams illustrating generally examples of different electrode configurations for measuring impedance-derived pulmonary and splanchnic fluid status signals and for providing neuromodulation therapy or other therapy to a splanchnic region of interest.

FIGS. 4A-4E are schematic diagrams illustrating generally examples of different electrode configurations that can be used such as for measuring impedance-derived pulmonary and splanchnic fluid status signals or for providing neuromodulation or other therapy such as to a splanchnic region of interest. FIGS. 4A-4E each illustrate a CFM device 105, including the can electrode 135 and the indifferent electrode 145 such as described above with respect to FIG. 1. FIG. 4A also illustrates the intravascular cardiac lead 110 including the tip electrode 120 and the ring electrode 125, and the splanchnic lead 112 including the tip electrode 196 and the ring electrode 194, such as described above with respect to FIG. 1.

In the example of FIG. 4A, a first region of interest ("ROI$_1$") is shown between the heart 115 and the device 105. ROI$_1$ represents area across which an impedance-derived measurement of pulmonary fluid associated with pulmonary edema can be measured, such as by using electrodes 120, 125, 135, and 145, such as to monitor pulmonary fluid status to be used to provide the first fluid status indicator. The second region of interest ("ROI$_2$") is shown between the splanchnic electrodes 194 and 196 and the device 105. ROI$_2$ represents an area across which a splanchnic impedance can be measured such as by using electrodes 194, 196, 135, and 145, such as to monitor the splanchnic fluid status to be used to provide the second fluid status indicator. FIG. 4A includes lead 400 including electrodes 402 and 404. The lead 400 and its associated electrodes can be used to provide therapy, such as neurostimulation therapy, to the splanchnic region, which can be controlled in response to one or both of the pulmonary fluid status information or the splanchnic fluid status information, such as described below.

Figure 4B:
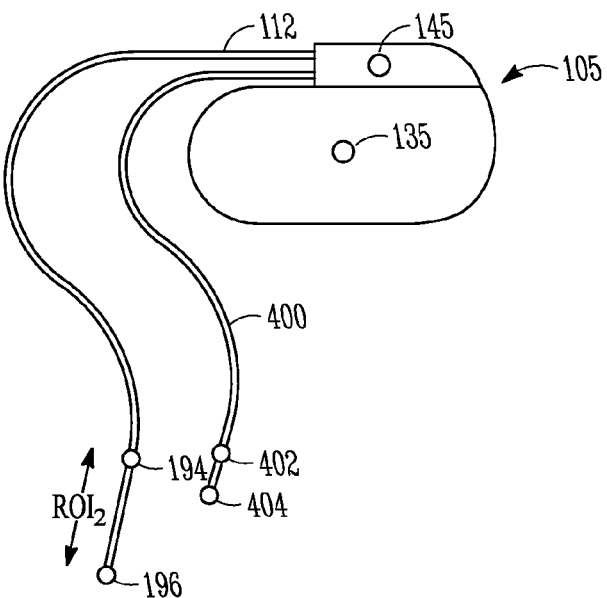

FIG. 4B illustrates an example of a splanchnic lead 112 with an electrode 194 located at or near a proximal end of the splanchnic region (e.g., closer to the device 105) and an electrode 196 located at or near a distal end of the splanchnic region (e.g., farther from the device 105). In this case, ROI$_2$ is between the electrodes 194 and 196. In an example, a splanchnic impedance can be measured using the electrodes 194 and 196, such as to both deliver an excitation signal (e.g., current) and to measure a responsive signal (e.g., voltage), from which impedance can be determined. The lead 400 and its associated electrodes 402 and 404 can be used to provide therapy, such as neurostimulation therapy, to the splanchnic region.

Figure 4C:
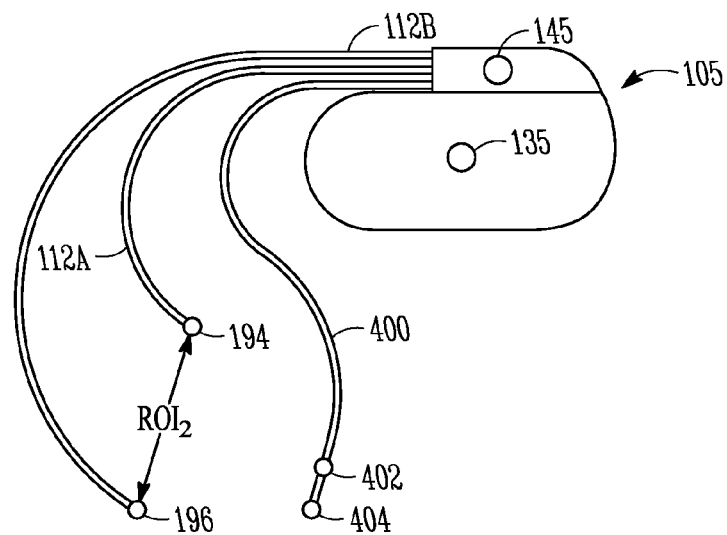

FIG. 4C illustrates an example of two splanchnic leads, such as a lead 112A and a lead 112B. The lead 112A includes an electrode 194, and the lead 112B includes an electrode 196. The ROI$_2$ in FIG. 4C can be the same as in FIG. 4B.

Splanchnic impedance can be measured such as by using the electrodes 194 and 196, such as described above with respect to FIG. 4B. However, in FIG. 4C the electrodes 194 and 196 are shown on different leads. The lead 400 and its associated electrodes 402 and 404 can be used to provide therapy, such as neurostimulation therapy, to the splanchnic region.

Figure 4D:
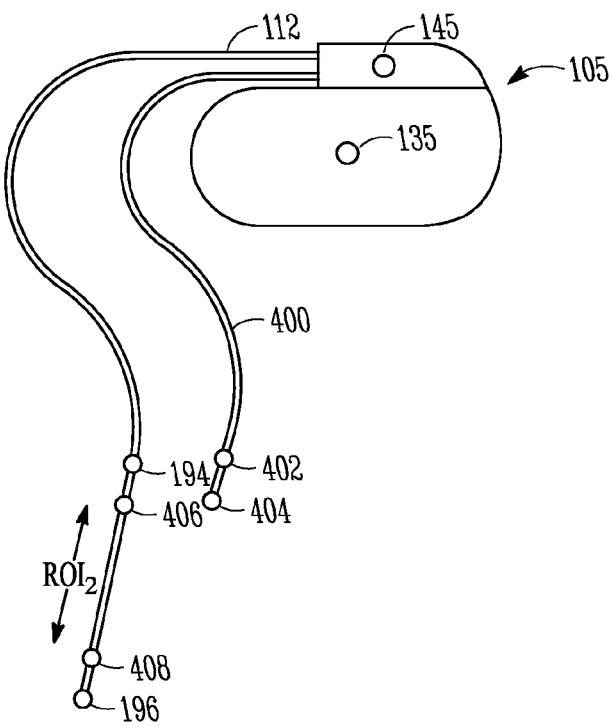

FIG. 4D illustrates an example of a splanchnic lead 112 including four different electrodes 194, 406, 408, and 196. The electrodes 194 and 506 can be located at or near the proximal end of the splanchnic region (e.g., closer to the device 105) and the electrodes 408 and 196 can be located at or near the distal end of the splanchnic region (e.g., farther from the device 105). The $ROI_2$ can be located in between the electrodes 406 and 408. In this example, splanchnic impedance can be measured such as by providing a current between the electrodes 194 and 196, and then sensing the responsive voltage between the electrodes 406 and 408. The lead 400 and its associated electrodes 402 and 404 can be used to provide therapy, such as neurostimulation therapy, to the splanchnic region.

Figure 4E:
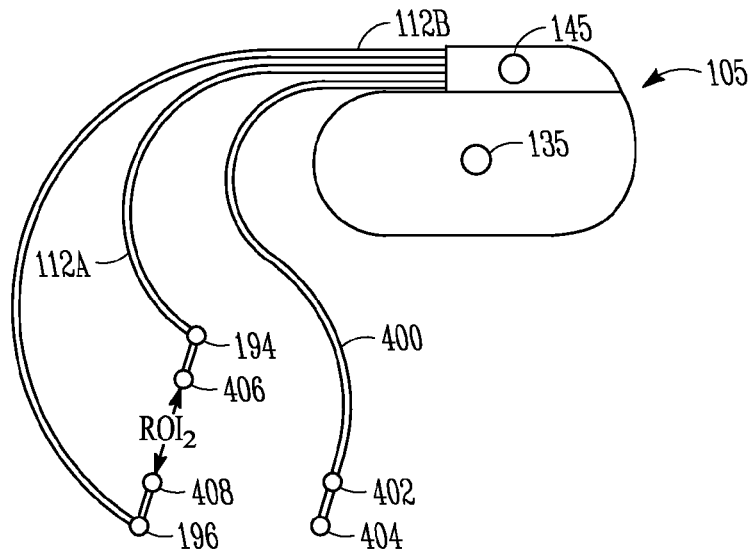

FIG. 4E illustrates an example of two splanchnic leads, such as a lead 112A and a lead 112B. The lead 112A can include the electrodes 194 and 406, and the lead 112B can include the electrode 196 and 408. The $ROI_2$ can be located in between electrodes 406 and 408, such as described above with respect to FIG. 4D. In this example, a splanchnic impedance can be measured such as by providing a current between the electrodes 194 and 196, and then sensing the responsive voltage between the electrodes 406 and 408. The lead 400 and its associated electrodes 402 and 404 can be used to provide therapy, such as neurostimulation therapy, to the splanchnic region.

Figure 5:
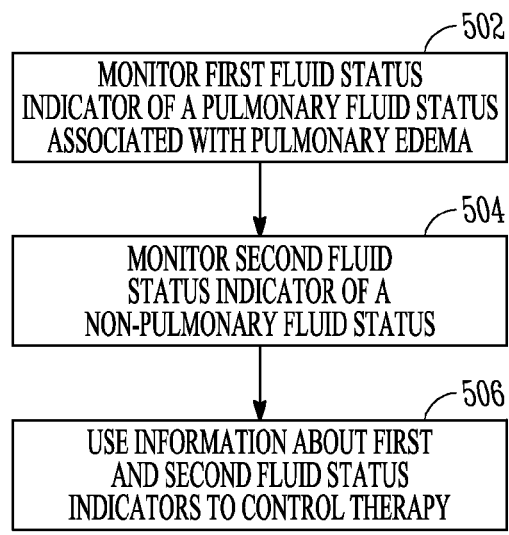
FIG. 5 is a chart illustrating an example of a method for controlling therapy for pulmonary edema by using both a pulmonary fluid status indicator and a non-pulmonary fluid status indicator.

FIG. 5 is a chart illustrating an example of a method for controlling therapy for pulmonary edema by using both a pulmonary fluid status indicator and a non-pulmonary fluid status indicator. At 502, a first fluid status indicator of a pulmonary fluid status associated with pulmonary edema is monitored. The first fluid status indicator can be derived from transthoracic impedance measurements. Monitoring of the first fluid status indicator using impedance-derived fluid measurements can be performed such as by using a first fluid status monitoring circuit including the exciter 250, the signal processor 255, and electrodes 120 and 125, for example. Monitoring of the first fluid status indicator can include distinguishing pulmonary fluid associated with pulmonary edema from pulmonary fluid associated with other disease states or etiologies, such as pleural effusion, for example. In order to monitor only pulmonary fluid associated with pulmonary edema, and not pulmonary fluid associated with pleural effusion, factors such as physiologic information, patient symptom information, and posture information can be used to specifically detect and monitor fluid associated with pulmonary edema, such as described in Stahmann et al. U.S. Patent Publication No. 2008/0108907 entitled "DETECTION OF PLEURAL EFFUSION USING TRANSTHORACIC IMPEDANCE," assigned to the assignee of the present patent application, the disclosure of which is incorporated herein by reference in its entirety.

In addition or alternative to using impedance-derived measurements to monitor the first fluid status indicator, pulmonary artery pressure measurements can be used to monitor the first fluid status indicator. Increased pulmonary artery pressure generally corresponds to increased pulmonary fluid due to pulmonary edema, and decreased pulmonary artery pressure generally corresponds to decreased pulmonary fluid. Pulmonary artery pressure can be measured, for example, by a separately implantable intravascular pulmonary artery pressure (PAP) sensor placed in the pulmonary artery to sense the PAP signal, such as that disclosed in the commonly assigned Stahmann U.S. Pat. No. 7,566,308, entitled "METHOD AND APPARATUS FOR PULMONARY ARTERY PRESSURE SIGNAL ISOLATION," which is hereby incorporated by reference in its entirety, including its disclosure of sensing the PAP signal using the implantable pressure sensor placed in the PA. In other examples, other pressure sensor configurations can be used to sense the PAP signal.

At 506, a second fluid status indicator of a non-pulmonary fluid status is monitored. Monitoring of the second fluid status indicator can be performed such as by using a second fluid status monitoring circuit including the exciter 250, the signal processor 255, electrodes 194 and 196, for example. Monitoring the second fluid status can include monitoring at least one of arterial blood pressure, splanchnic impedance, skeletal muscle impedance, or skin impedance. Monitoring splanchnic impedance, for example, involves monitoring an impedance-derived or other measurement representative of fluid status associated with a splanchnic organ or a splanchnic region.

The splanchnic impedance can be measured either (1) directly, within the splanchnic region, or (2) indirectly, such as across both a splanchnic and thoracic region, then subtracting a separate measurement of the impedance across the thoracic region. Splanchnic impedance in $ROI_2$ can be directly measured using the electrodes 506 and 508 shown in FIG. 4D. Splanchnic impedance can be indirectly measured by measuring a pulmonary and splanchnic first impedance, such as using electrodes 194, 196, 135, and 145 (in a four-electrode example of delivering excitation and measuring a response, such as shown in FIG. 4A), and measuring a corresponding pulmonary-only second impedance in $ROI_1$, such as by using electrodes 120, 125, 135, and 145 (in a similar four-electrode example, such as shown in FIG. 4A). By taking a difference between the pulmonary and splanchnic first impedance and the pulmonary-only second impedance, the splanchnic impedance can be indirectly obtained.

At 506, information about the first and second fluid status indicators can be used to provide an alert to a user or automated process, or to control a therapy for treating pulmonary edema. The therapy can be aimed at adjusting at least one of the first fluid status (e.g., pulmonary fluid status) or the second fluid status (e.g. non-pulmonary fluid status). In an example, the controller 265 can be used to control therapy using information about the first and second fluid status indicators. In an example, the controller 265 can be configured to control therapy using other information, such as HF decompensation alert information or information about a physiological parameter, in addition to information about the first and second fluid status indicators. In an example, the controller 265 can be configured to control therapy without using information about the first and second fluid status indicators, such as when therapy is provided for a specified period of time on an intermittent basis to a subject with chronic HF.

Controlling a therapy can include triggering or adjusting the therapy in response to an increase in a pulmonary fluid status indicator associated with pulmonary edema. Controlling a therapy can include triggering or adjusting the therapy in response to a decrease in a splanchnic fluid status indicator below a specified threshold value. A decrease in the splanchnic fluid status indicator can indicate improper fluid distribution in the subject, including an increase in pulmonary fluid due to pulmonary edema. Therapy can be provided constantly or at specified intervals. Therapy can be provided more frequently when pulmonary edema is indicated by the pulmonary or splanchnic fluid status indicators. Furthermore, the therapy can include neuromodulation therapy, drug therapy, or a vessel blood flow control therapy. Such therapies can be used to control vasodilation or vasoconstriction in a localized vascular region of the subject, thereby adjusting at least one of the pulmonary fluid status or the non-pulmonary fluid status (e.g. splanchnic fluid status).

Neuromodulation therapy modulates the function of the autonomic nervous system, rather than providing direct electrostimulation to the heart to evoke depolarizations resulting directly from the electrostimulations. The autonomic nervous system (ANS) regulates "involuntary" organs, while the contraction of voluntary (skeletal) muscles is controlled by somatic motor nerves. Examples of involuntary organs include respiratory and splanchnic organs, and include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure (e.g. by causing vasoconstriction) and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure (e.g. by causing vasodilation) and heart rate, and increases digestion to conserve energy. The ANS maintains normal internal function and works with the somatic nervous system.

Neural stimulation can be used to stimulate or increase nerve traffic, or to inhibit or decrease nerve traffic. An example of neural stimulation to stimulate nerve traffic can use a lower frequency signal (e.g., within a range on the order of 20 Hz to 50 Hz). An example of neural stimulation to inhibit nerve traffic can use a higher frequency signal (e.g., within a range on the order of 120 Hz to 150 Hz). Other methods for stimulating and inhibiting nerve traffic can be used.

In an example, neuromodulation therapy can be provided to a celiac ganglion, which is one of two large nerve masses in the upper abdomen that innervates the splanchnic organs. The celiac ganglia are part of the sympathetic division of the autonomic nervous system, and they innervate most of the digestive tract. High frequency neural stimulation can be provided to a celiac ganglion, such as through electrodes coupled to a lead running from a CFM device through the inferior vena cava to the celiac ganglion. Such neural stimulation can inhibit nerve traffic in the sympathetic nerves of the celiac ganglia, resulting in vasodilation of the vascular beds in and around the splanchnic organs. It is believed that vasodilation of these high-capacitance splanchnic vascular beds can result in a redistribution of blood volume, such that blood flow to the splanchnic region is increased and, as a result, blood volume in the in the pulmonary region is decreased. Decreased blood volume in the pulmonary region can, in turn, cause a decrease in pulmonary fluid associated with pulmonary edema.

In an example, neuromodulation therapy can be provided directly to nerves of the spinal cord, such as at the level of the fifth and sixth thoracic vertebrae ("T5" to "T6"), where nerves that innervate splanchnic organs can be located. Neural stimulation can be provided to the spinal cord, such as through electrodes coupled to a lead running from a CFM device through the subclavian vein and thoracic duct to the T5/T6 region of the spinal cord. The spinal cord contains both sympathetic and parasympathetic nerves. Using low frequency neural stimulation to stimulate the parasympathetic nerves or high frequency neural stimulation to inhibit the sympathetic nerves can result in vasodilation of the vascular beds in and around the splanchnic organs. As described above, it is believed that vasodilation of the splanchnic vascular beds can result in redistribution of blood away from the pulmonary vascular beds, thereby reducing pulmonary edema.

Neuromodulation can be provided to the spinal cord at a lower level, such as at the level of fourth lumbar vertebrae ("L4"). Nerves emerging from the spinal cord at the L4 level can include those that innervate the skeletal muscle in the leg. Like the splanchnic vascular beds, the vascular beds in skeletal muscle are generally high capacitance, allowing for large increases in blood flow. Thus, it is believed that neuromodulation causing vasodilation of the vascular beds of skeletal muscle in the leg can be used to treat pulmonary edema via redistribution of blood flow as described above.

Furthermore, neuromodulation can be provided to parasympathetic splanchnic nerves, such as by stimulation or inhibition of the vagal nerve at or below the esophageal plexus, for example. Neuromodulation can be provided via a nerve cuff or via transvenous or translymphatic stimulation/inhibition. Neuromodulation can be provided by stimulating or inhibiting the adrenal nerve to modulate sympathetic tone. Baroreceptor stimulation or inhibition is another example of providing neuromodulation.

In an example, therapy resulting in localized vasodilation or vasoconstriction can be controlled concurrently in at least two separate localized vascular regions. This can result in an adjustment of fluid balance between the two separate localized regions. For example, localized vasodilation therapy can be provided to the splanchnic region while localized vasoconstriction therapy is provided to the skeletal muscle in the leg. It is believed that such a redistribution of blood volume can cause decreased blood volume in the pulmonary vascular beds, thereby alleviating pulmonary edema. Furthermore, it is believed that targeting two separate localized regions concurrently, such as by causing vasodilation at one region and vasoconstriction at the other region, can prevent a decrease or increase in systemic blood pressure that might occur as a result of targeting therapy to a single region.

In an example, controlling the therapy to adjust at least one of a pulmonary fluid status or a non-pulmonary fluid status can include inhibiting the therapy. Therapy can be inhibited after being provided for a specified period of time, for example. Therapy can be reduced or inhibited in response to a decrease in the pulmonary fluid status indicator below a specified threshold value. In this case, therapy would no longer be needed because the pulmonary edema has improved. Therapy can be inhibited in response to an increase in the pulmonary fluid status indicator above a specified threshold value. In this case, the therapy would be discontinued because it failed to effectively treat the pulmonary edema. Therapy can be reduced or stopped in response to an increase in the non-pulmonary fluid status indicator above a specified threshold value. In this case, blood has already been redistributed to the non-pulmonary region, and further redistribution to that region could result in peripheral edema or other adverse events. Finally, therapy can be stopped in response to a decrease in the non-pulmonary fluid status indicator below a specified threshold value. In this case, further treatment could result in hypotension or hypoperfusion of organs, regardless of whether the pulmonary edema has been resolved. Any combination of the above fluid status increases or decreases beyond specified thresholds could be used to terminate therapy.

In an example, controlling the therapy to adjust at least one of a pulmonary fluid status or a non-pulmonary fluid status can include synchronizing the delivery of the therapy with a specified portion of the subject's cardiac cycle. For example, the delivery of therapy can be synchronized with a systolic portion of the subject's cardiac cycle. This can help reduce afterload in patients with HF, which results in less stress being placed on a weakened heart muscle. Similarly, the delivery of therapy could be synchronized with other portions of the subject's cardiac cycle, such as the occurrence of diastole or a particular waveform, including the P wave, the T wave, or the QRS complex.

Therapy can be provided on an acute or chronic basis. In an example, acute therapy can be triggered in response to information about the first and second fluid status indicators, a decompensation alert, a patient-initiated alert, or a physician's input. For example, a decompensation alert can be issued by a CFM device based on decreased pulmonary fluid impedance, elevated pulmonary artery pressure, or elevated splanchnic impedance, each of which can suggest the presence of pulmonary edema. Other examples of decompensation alerts can include those based on heart rate information, respiration rate information, respiration timing information, blood pressure information, lung tidal volume information, weight information, intrathoracic impedance information (e.g., to assess fluid build-up, to monitor respiration-related parameters, or to monitor cardiac-related parameters), heart sound timing information, heart sound magnitude information (e.g., an S3 heart sound magnitude), or other information (e.g., a response to a user query regarding physiologic information). HF decompensation alerts can be based on information obtained from an intra-abdominal pressure sensor, such as described in Hatlestad et al. U.S. Provisional Patent Application No. 61/096,364 entitled "CHRONICALLY IMPLANTED ABDOMINAL PRESSURE SENSOR FOR CONTINUOUS AMBULATORY ASSESSMENT OF RENAL FUNCTIONS," assigned to the assignee of the present patent application, the disclosure of which is incorporated herein by reference in its entirety. Further discussion of physiologic signs and symptoms that can be used to detect HF decompensation and trigger HF decompensation alerts, can be found in Siejko et al. U.S. Provisional Patent Application No. 61/098,858 entitled "SYSTEM AND METHOD FOR DETECTION OF HF DECOMPENSATION BASED ON SIGNS AND SYMPTOMS," assigned to the assignee of the present patent application, the disclosure of which is incorporated herein by reference in its entirety. In an example, acute therapy can be controlled such that it is provided in response to a decompensation alert having been issued. This can help to ensure that the therapy is being provided only when a subject is exhibiting acute HF decompensation. Acute therapy can be delivered constantly, such as for up to 24 hours or until the subject's first and second fluid status indicators or other physiological parameters have returned to baseline.

Therapy can be delivered on a chronic basis. In an example, chronic therapy can be provided only if a decompensation alert has not been issued within a specified preceding time period. This can help ensure that the chronic therapy is only being provided to patients with chronic HF, not to an acute patient who can require immediate attention by a physician. Chronic therapy can include intermittent therapy, such as therapy provided for 15 minutes per day, for example. In addition to using information about the first and second fluid status indicators to control chronic therapy, other information about a patient parameter can be used to control the therapy. For example, the subject's posture can be detected using a posture sensing apparatus, such as described in Wang et al. U.S. Pat. No. 7,471,290 entitled "POSTURE DETECTION SYSTEM" assigned to the assignee of the present patent application, the disclosure of which is incorporated herein by reference in its entirety. Therapy can be controlled such that, in an example, it is only provided when the subject is in a recumbent position. A recumbent position can be determined as an angle of reclination that is a specified number of degrees (e.g., 65 degrees) away from vertical. HF patients with pulmonary edema are generally unable to tolerate a recumbent position because their lungs fill with fluid and make it difficult to breathe. Consequently, acute or unstable HF patients may use several pillows to sleep, or they may sleep in an upright position, which helps limit the amount of fluid pooling in the pulmonary circulation and/or lungs. Therefore, controlling the therapy such that it is only provided when the subject is in a recumbent position can be a way of ensuring that this method of treatment is only used for subjects suffering from chronic HF, not those who have an acute worsening of HF and pulmonary edema, which can require immediate hospitalization. In addition, controlling the therapy such that it is only provided when the subject is in a recumbent position can be helpful in preventing gravity from interfering with the therapy-induced redistribution of blood.

In addition to posture, a patient physical activity level can be used, together with information about the first and second fluid status indicators, to control chronic therapy. For example, a subject's physical activity level can be detected using an accelerometer. Therapy can be controlled such that, in an example, it is only provided when the subject's physical activity level is below a specified threshold value. This can help ensure that therapy is provided when the patient is at rest or asleep, in an example. Providing therapy when the patient is resting or sleeping can be helpful in order to avoid shifts in gravitational forces or changes in metabolic demand that could interfere with the redistribution of blood volume. To determine when a patient is sleeping, a sleep detector can be included. One example of a sleep detector is described in Carlson et al., U.S. patent application Ser. No. 09/802,316, now U.S. Pat. No. 6,678,547, entitled "CARDIAC RHYTHM MANAGEMENT SYSTEM USING TIME-DOMAIN HEART RATE VARIABILITY INDICIA," which is assigned to Cardiac Pacemakers, Inc., and which is incorporated herein by reference in its entirety, including its description of a sleep detector. Another example of a sleep detector is described in Hatlestad et al., U.S. Patent Publication No. 2004/0073128, now U.S. Pat. No. 7,226,422, entitled "DETECTION OF CONGESTION FROM MONITORING PATIENT RESPONSE TO RECUMBENT POSITION," which is assigned to Cardiac Pacemakers, Inc., and which is incorporated herein by reference in its entirety.

Acute or chronic therapy can be monitored using the first and second fluid status indicators. Thus, as shown in FIG. 5, the first and second fluid status indicators can continue to be monitored after providing or controlling the therapy, such as to evaluate whether or not the therapy is working to treat pulmonary edema. In addition, therapy can be monitored via alert sensor feedback or patient feedback.

Further Examples, Such As For Cardiac Conditioning

Another application can include cardiac conditioning therapy, such as which can be provided by intermittent periods of cardiac blood volume redistribution. The present inventors have recognized that short periods of blood flow redistribution between the heart and other high fluid-capacitance systemic vascular beds, such as those in the splanchnic organs, skeletal muscle, or skin, may be beneficial for HF patients.

A temporary increase in cardiac blood volume may help in stretching of the myocardium. Myocardial stretch can confer therapeutic benefit, for example, by inducing the release of atrial natriuretic peptide (ANP) from the atria and brain natriuretic peptide (BNP) from the ventricles. ANP is a hormone that can cause vasodilation and diuresis in response to increased blood pressure and volume. ANP can help inhibit hypertrophy and fibrosis of the myocardium—often referred to as "remodeling" which can occur during or after an ischemic event, for example. It is also believed that ANP and BNP can inhibit the renin-angiotensin-aldosterone system (RAAS), thereby preventing or inhibiting maladaptive cardiac remodeling. Thus, ANP and BNP can benefit HF patients by reducing the stress of blood volume overload on the heart, as well as inhibiting cardiac remodeling.

The present inventors have recognized that the release of ANP and BNP can be augmented by temporarily creating excess blood volume in the heart, such as by increasing cardiac preload or afterload or both, thereby causing stretch of the myocardium. Temporary redistribution of blood toward the heart can be achieved, for example, by targeted localized vasoconstriction of systemic arterioles, or a targeted localized decrease in venous capacitance or decrease in venous resistance. These targeted vessel responses can be effected through localized neuromodulation, for example, such as similar to that described above. In an example, the temporary blood redistribution therapy can be administered for about fifteen minutes per day, for example, such as during three five-minute sessions per day.

An implantable medical device, similar to CFM device 105 illustrated in FIG. 1, can be used to provide the above described cardiac conditioning therapy. In an example, four or more electrodes, similar to electrode 120 or 125, can be disposed in the multiconductor lead 110 located within the heart, such as within the right ventricle of the heart 115. A multiconductor lead 112, disposed in the splanchnic region between T5 and T12, and electrodes 194 and 196, can be configured as described above with respect to FIG. 1.

The device 105 can be configured similarly to the above description with respect to FIG. 2. In an example, the response signal sensed by the signal processor 255 can be a voltage that represents an intracardiac (e.g., across at least a portion of the heart) or a splanchnic (e.g. across at least a portion of a splanchnic organ) impedance. An example of an approach for measuring intracardiac impedance is described in Citak et al. U.S. Pat. No. 4,773,401 entitled "PHYSIOLOGIC CONTROL OF PACEMAKER RATE USING PRE-EJECTION INTERVALS AS THE CONTROLLING PARAMETER," assigned to the assignee of the present application, the disclosure of which is incorporated herein by reference in its entirety, including its description of an approach for measuring intracardiac impedance.

In an example, an impedance-derived cardiac blood volume status indicator can be obtained such as by measuring intracardiac (within the heart) impedance. For example, an intracardiac impedance can be measured to obtain a cardiac blood volume status indicator of a cardiac blood volume status, wherein an increase in the cardiac blood volume status indicator correlates to an increase in cardiac blood volume. In an example, an impedance-derived cardiac blood volume status indicator can be obtained by measuring stroke impedance, which is a component of intracardiac impedance. Stroke impedance is representative of the change in blood volume in the heart during a cardiac cycle. Stroke impedance can be derived from intracardiac impedance, for example, by taking the difference between the highest and lowest measured values of intracardiac impedance. In an example, an impedance-derived cardiac blood volume status indicator can be obtained by measuring transthoracic impedance, such as to provide a pulmonary impedance based indicator of cardiac blood volume status. Transthoracic impedance can be measured such as described above with respect to FIG. 3.

The cardiac blood volume status indicator can be monitored by a cardiac blood volume status monitoring circuit, which can include the exciter 250, the signal processor 255, and electrodes such as the electrodes 120 and 125, for example. In addition, a splanchnic blood volume can be measured to obtain a splanchnic blood volume status indicator of a splanchnic blood volume status, wherein an increase in the splanchnic blood volume status indicator correlates to an increase in the splanchnic blood volume. The splanchnic blood volume status indicator can be monitored by a splanchnic blood volume status monitoring circuit, which can include the exciter 250, the signal processor 255, and electrodes such as the electrodes 194 and 196, for example.

The controller 265 can be configured to use information about the cardiac blood volume status indicator or the splanchnic blood volume status indicator, or both, to control therapy provided by the therapy circuit 270, in an example. The therapy provided by the therapy circuit 270 can temporarily adjust one or both of the cardiac blood volume status or the splanchnic volume status. An example of a therapy that can be provided by the therapy circuit 270 can include neuromodulation therapy provided to the splanchnic region, similar to that described above. The therapy circuit 270 can provide neuromodulation resulting in localized splanchnic vasoconstriction, which, in turn, can decrease splanchnic blood volume and increase cardiac blood volume. The therapy circuit 270 can provide neuromodulation resulting in localized splanchnic vasodilation, which, in turn, can increase splanchnic blood volume and decrease cardiac blood volume.

In an example, the controller 265 can be configured to use other information, in addition to or in place of information about the cardiac and splanchnic blood volume status indicators, to control therapy provided by the therapy circuit 270. Examples of such information include heart rate, cardiac stroke volume, cardiac contractility, arterial blood pressure, and venous blood pressure. These physiologic indicators can be used to identify instances in which it may not be favorable to temporarily increase cardiac blood volume in order to provide conditioning therapy. For example, increased heart rate, decreased stroke volume, decreased contractility, decreased arterial blood pressure, increase venous blood pressure, or any combination of the above, can indicate a weakened or impaired cardiac state. Under these conditions, the heart may not be able to compensate for a transient increase in blood volume, and the patient may not be able to benefit from the conditioning therapy. Therefore, the controller 265 can adjust the amount of neuromodulation provided to the splanchnic region by the therapy circuit 270 in response to an increase in heart rate above a first specified threshold value, a decrease in cardiac stroke volume below a second specified threshold value, a decrease in the measurement of cardiac contractility below a third specified threshold value, a decrease in arterial blood pressure below a fourth specified threshold, an increase in venous blood pressure above a fifth specified threshold, or any combination of two or more of the above. In the presence of one or more such physiologic indicators, the controller 265 can be configured to decrease an amount of sympathetic nerve stimulation to the splanchnic region, increase an amount of sympathetic nerve inhibition to the splanchnic region, increase an amount of parasympathetic nerve stimulation to the splanchnic region, decrease an amount of parasympathetic nerve inhibition to the splanchnic region, or do any combination of two or more of the above. It is believed that the effect of such neuromodulation therapy can be an increase in splanchnic blood volume and a decrease in cardiac blood volume, which could reduce the load on a weakened or impaired heart.

In the example shown in FIG. 2, the therapy circuit 270 can be included within the cardiac function management device 105. In other examples, the therapy circuit 270 can be part of a separate implanted or external device. If the therapy circuit 270 is part of a separate device, the device 105 can communicate with the therapy circuit. This can include direct communication between two devices in or on the human body, wherein such communication can be carried out within the human body, such as via inductive coupling, ultrasonic communication, or using body tissue as an electrical conductor, as illustrative examples. It can additionally or alternatively include indirect communication between two implanted devices, or between an implanted and an external device, such as by using a local or remote external device as an intermediary for performing the communication, such as via inductive, RF, or other telemetry. An illustrative example can include communicating between an implanted device 105 and a therapy circuit located in a separately implanted device, such as by using the Boston Scientific Corp. (Cardiac Pacemakers, Inc.) LATITUDE® System, which can automatically collect information from a subject's implanted medical device 105 and communicate the information to a another one of the subject's implanted or ambulatory personal medical device, such as via a local external interface 290 that can be communicatively coupled via a communication network 294 to a secure remote computer 292.

The signal processor 255 can be configured similarly to that described above with respect to FIG. 3. However, a bandpass filter can be used in place of the lowpass filter 355, such as to pass a heart contraction component of the intracardiac impedance signal instead of the lower frequency pulmonary edema or similar fluid status component of the thoracic impedance signal. (However, the lowpass filter 355 can still be included, such as to pass a lower frequency fluid status component of a splanchnic impedance signal). In addition, a blood volume status calculation module can be used in place of the fluid status calculation module 340. The blood volume status calculation module can receive an output signal from the bandpass filter, and can provide a resulting blood volume status indication at node 260 to the controller 265, such as explained below. In an example, a blood volume status calculation module can be implemented as a sequence of instructions executed on or otherwise performed by a microprocessor. In an example, the blood volume status calculation module can be implemented as any other hardware or software configuration capable of calculating a blood volume status indicator based on impedance-derived blood volume status information.

In an example, the blood volume status calculation module can include a comparator, such as for comparing the bandpass-filtered intracardiac or lowpass-filtered splanchnic impedance signals to a respective threshold value. An output of the comparison can be used to provide a respective blood volume status indicator, for example, indicating excess blood in the particular region when its impedance falls below a specified threshold value. In an example, the specified threshold value can be specified using a long-term or other baseline value of the impedance, such as obtained from the subject during a normal condition (e.g., no cardiac blood volume overload). For example, the specified threshold value can be specified as an offset from such normal condition value. In an example, the specified threshold value can be specified using a value obtained during abnormal conditions, such as during a decompensation episode, or a time period preceding an associated decompensation episode.

In an example, a difference or ratio between a long-term average (or other baseline measure of central tendency) and a short-term average (or other more acute measure of central tendency) can be used as a blood volume status indication, or compared to a threshold value or otherwise signal-processed to obtain a resulting blood volume status indication.

The controller 265 can be configured to adjust an amount of neuromodulation (provided by the therapy circuit 270) to the splanchnic region when the cardiac blood volume status indicator is below a specified threshold value. For example, the controller 265 can be configured to increase an amount of sympathetic nerve stimulation to the splanchnic region when the cardiac blood volume status indicator is below the specified threshold value. In an example, the controller 265 can be configured to decrease an amount of sympathetic nerve inhibition to the splanchnic region when the cardiac blood volume status indicator is below the specified threshold value. In an example, the controller 265 can be configured to decrease an amount of parasympathetic nerve stimulation to the splanchnic region when the cardiac blood volume status indicator is below the specified threshold value. In an example, the controller 265 can be configured to increase an amount of parasympathetic nerve inhibition to the splanchnic region when the cardiac blood volume status indicator is below the specified threshold value. It is believed that any of the above neuromodulation therapies, alone or in combination, can result in decreased splanchnic blood volume and increased cardiac blood volume.

The controller 265 can be configured to adjust an amount of neuromodulation (provided by the therapy circuit 270) to the splanchnic region when the cardiac blood volume status indicator is above a specified threshold value. For example, the controller 265 can be configured to decrease an amount of sympathetic nerve stimulation to the splanchnic region when the cardiac blood volume status indicator is above the specified threshold value. In an example, the controller 265 can be configured to increase an amount of sympathetic nerve inhibition to the splanchnic region when the cardiac blood volume status indicator is above the specified threshold value. In an example, the controller 265 can be configured to increase an amount of parasympathetic nerve stimulation to the splanchnic region when the cardiac blood volume status indicator is above the specified threshold value. In an example, the controller 265 can be configured to decrease an amount of parasympathetic nerve inhibition to the splanchnic region when the cardiac blood volume status indicator is above the specified threshold value. It is believed that any of the above neuromodulation therapies, alone or in combination, can result in increased splanchnic blood volume and decreased cardiac blood volume.

In an example, the controller 265 can be configured to adjust an amount of neuromodulation (provided by the therapy circuit 270) to the splanchnic region in response to a decrease in transthoracic impedance that is suggestive of pulmonary edema and blood volume overload in the heart. For example, in response to a decrease in transthoracic impedance, the controller can be configured to decrease an amount of sympathetic nerve stimulation to the splanchnic region, increase an amount of sympathetic nerve inhibition to the splanchnic region, increase an amount of parasympathetic nerve stimulation to the splanchnic region, decrease an amount of parasympathetic nerve inhibition to the splanchnic region, or do any combination of the above. It is believed that any of the above neuromodulation therapies, alone or in combination, can result in increased splanchnic blood volume and decreased cardiac blood volume, thereby alleviating the cardiac blood volume overload.

In an example, the device 105 can provide cardiac blood volume redistribution therapy via a pacing circuit that can be coupled to the controller 265. The controller 265 can be configured to control the pacing circuit to issue pacing pulses that are unsynchronized to an intrinsic contraction or triggered to be offset enough from the intrinsic contraction to provide stretch to a portion of the myocardium. Such pacing therapy can be provided by the therapy circuit 270 in addition to or in place of neuromodulation therapy.

In an example, the device 105 can be configured to use cardiac blood volume redistribution therapy to inhibit prevent atrial tachyarrhythmias. It is believed that an increase in end diastolic pressure due to reduced cardiac output or valvular dysfunction can cause increased stretching of the atria, which may lead to atrial tachyarrhythmia. Furthermore, it is believed that reducing blood volume in the left side of the heart can help to alleviate atrial stretch and thus inhibit or prevent atrial arrhythmias. In an example, the device 105 can include an atrial proarrhythmia condition sensor that can be coupled to the controller 265. The atrial proarrhythmia sensor can be configured to sense a change in electrocardiogram morphology change, a change in heart rate, or a change in heart rate regularity, in an example. The controller 265 can be configured to control the delivery of neuromodulation by the therapy circuit 270 to the splanchnic region in response to the detection of an atrial proarrhythmia condition. In an example, the therapy circuit 270 can be configured to deliver neuromodulation to the splanchnic region in association with an anti-tachyarrhythmia therapy, such as defibrillation or anti-tachyarrhythmia pacing (ATP). Examples of neuromodulation therapy that can be delivered in response to an atrial proarrhythmia condition include: increasing an amount of parasympathetic nerve stimulation, decreasing an amount of parasympathetic nerve inhibition, increasing and amount of sympathetic nerve inhibition, or decreasing an amount of sympathetic nerve stimulation. These examples of neuromodulation can lead to an increase in splanchnic blood volume and a decrease in cardiac blood volume. Neuromodulation can be discontinued upon successful cardioversion after anti-tachyarrhythmia therapy or when the atrial proarrhythmia condition is no longer detected.

The electrode configurations used to provide cardiac blood volume redistribution therapy can be similar to those described above with respect to FIGS. 4A-4E, but with $ROI_1$ being between two different electrodes located within the heart.

Figure 6:
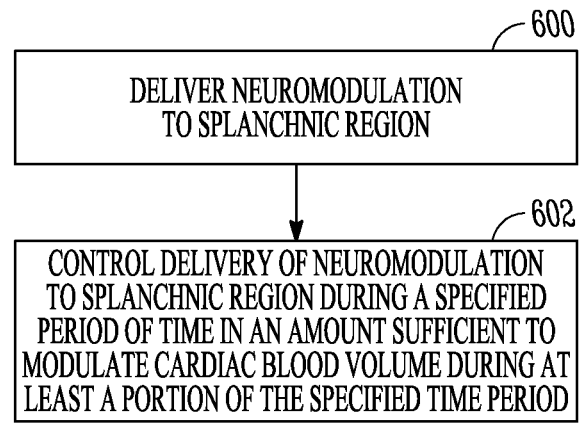
FIG. 6 is a chart illustrating generally an example of a method for providing cardiac conditioning therapy by delivering neuromodulation to a splanchnic region to modulate cardiac blood volume.

FIG. 6 is a chart illustrating generally an example of a method for providing cardiac conditioning therapy by delivering neuromodulation to a splanchnic region to modulate cardiac blood volume. At 600, neuromodulation therapy can be delivered to a splanchnic region. An example of the delivery of neuromodulation therapy to the splanchnic region is described above with respect to FIG. 5. Electrical activation (e.g., stimulation) of nerves can involve the controlled and targeted release of neurotransmitters. Some neurotransmitters, such as neuropeptide Y and norepinephrine, can cause vasoconstriction, and some such as ATP and acetylcholine (ACh), can cause vasodilation. It can be possible for the same nerve to release different neurotransmitters under different stimulation protocols and therefore elicit widely ranging functional responses of the target vessel or organ. Moreover, the type of receptors that neurotransmitters bind to can determine the functional response of the vessel. For example, ACh can cause vasodilation of skeletal muscle vasculature but constriction in the coronary circulation. Therefore, while stimulation of sympathetic fibers generally causes vasoconstriction, it is possible that it can cause vasodilation.

At 602, the delivery of neuromodulation to the splanchnic region can be controlled during a specified period of time in an amount sufficient to modulate cardiac blood volume during at least a portion of the specified time period. As described above with respect to FIG. 5, controlling the delivery of neuromodulation to the splanchnic region can include providing localized splanchnic vasoconstriction therapy or localized splanchnic vasodilation therapy. It is believed that intermittent vasoconstriction, followed by vasodilation, of the splanchnic vascular beds can result in temporary loading, followed by unloading, of the heart with blood. It is believed that vasoconstriction of the splanchnic vascular beds causes cardiac loading because blood redistributes from the splanchnic region to the heart. Similarly, it is believed that vasodilation of the splanchnic vascular beds causes cardiac unloading because blood redistributes from the heart to the splanchnic region. This intermittent loading and unloading of the heart can cause myocardial stretch, leading to the release of ANP and/or BNP from cardiac cells, as described above. In an example, splanchnic vasoconstriction can be provided for periods of about 20-30 minutes per day. Such intermittent short duty cycles of splanchnic vasoconstriction/vasodilation can enhance the effects of cardiac blood volume redistribution and the resulting myocardial stretch.

In an example, the method illustrated in FIG. 6 can further include monitoring heart rate, cardiac stroke volume, or cardiac contractility. If, during volume redistribution therapy, there is a decrease in stroke volume, a decrease in contractility, a dramatic rise in heart rate, a decrease in arterial blood pressure, or an increase in venous blood pressure, neuromodulation can be adjusted or discontinued, such as to avoid placing excess stress on a weakened heart. Such a weakened heart may not be able to compensate for the increased preload provided during redistribution therapy. Neuromodulation can be adjusted, for example, by decreasing sympathetic nerve stimulation to the splanchnic region, increasing sympathetic nerve inhibition to the splanchnic region, increasing parasympathetic nerve stimulation to the splanchnic region, or decreasing parasympathetic nerve inhibition to the splanchnic region. Such adjustment of the neuromodulation can cause splanchnic vasodilation, and, in turn, decreased cardiac blood volume. This can help to alleviate stress on the heart.

In an example, the method illustrated in FIG. 6 can further include transiently delivering cardiac pacing pulses that are unsynchronized to an intrinsic contraction, or offset enough from the intrinsic contraction, to provide a stretch to a portion of the myocardium. For example, short AVD or VVI mode pacing can be provided so that the heart beats asynchronously, leading to increased atrial or ventricular blood volume and, in turn, increased stretch in the respective chambers. Transient stretching can lead to cardiac conditioning through the release of ANP and/or BNP, as described above.

In an example, the method illustrated in FIG. 6 can include detecting an atrial proarrhythmia condition and delivering neuromodulation to the splanchnic region in response to the detection of an atrial proarrhythmia condition. An example of an atrial proarrhythmia condition is an increase in end diastolic pressure due to reduced cardiac output or valvular dysfunction. An increase in end diastolic pressure can cause increased stretching of the atria and lead to atrial tachyarrhythmias. It is believed that by redistributing blood in away from heart and toward the splanchnic region, atrial stretch can be alleviated and arrhythmias can be prevented. In an example, redistribution therapy such as neuromodulation can be triggered during a sensed atrial arrhythmia. Additionally, such redistribution therapy can be provided in association with anti-tachyarrhythmia therapy, such as defibrillation or anti-tachyarrhythmia pacing. Examples of neuromodulation therapy that can be delivered in response to a sensed atrial arrhythmia or a an atrial proarrhythmia condition include: increasing an amount of parasympathetic nerve stimulation, decreasing an amount of parasympathetic nerve inhibition, increasing and amount of sympathetic nerve inhibition, or decreasing an amount of sympathetic nerve stimulation. These examples of neuromodulation can lead to an increase in splanchnic blood volume and a decrease in cardiac blood volume. Neuromodulation can be discontinued upon successful cardioversion after anti-tachyarrhythmia therapy or when the atrial proarrhythmia condition is no longer detected.

Figure 7:
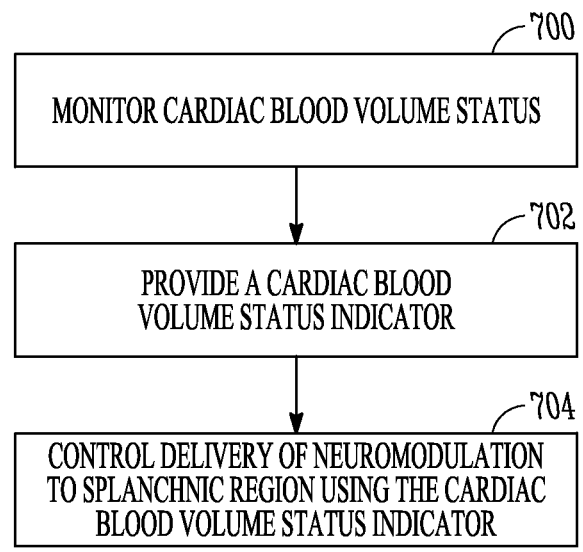
FIG. 7 is a chart illustrating an example of a method for providing cardiac conditioning therapy using a cardiac blood volume status indicator.

FIG. 7 is a chart illustrating an example of a method for providing cardiac conditioning therapy using a cardiac blood volume status indicator. At 700, cardiac blood volume status is monitored. Monitoring cardiac blood volume status can be accomplished by monitoring an intracardiac impedance, for example. An example of a method for measuring intracardiac impedance is described in Citak et al., cited above. Monitoring cardiac blood volume status can be accomplished by monitoring a transthoracic impedance measurement indicative of pulmonary impedance. For example, a decrease in pulmonary impedance below a specified threshold can be indicative of pulmonary edema, which, in turn, can suggest a cardiac volume overload. Furthermore, in an example, the monitoring of cardiac blood volume status can be accompanied by monitoring of a splanchnic blood volume status. In this example, information about both the cardiac blood volume status and the splanchnic blood volume status can be used to control blood redistribution therapy.

At 702, a cardiac blood volume status indicator is provided using the monitored cardiac blood volume status data. The cardiac blood volume status indicator can be based on intracardiac impedance. In an example, the cardiac blood volume status indicator can be based on stroke impedance, a measurement which can be derived from intracardiac impedance, such as by taking the difference between the highest and lowest measured values of intracardiac impedance. Stroke impedance represents the change in blood volume in the heart during a cardiac cycle.

At 704, the delivery of neuromodulation to a splanchnic region is controlled using the cardiac blood volume status indicator, such as in a closed-loop feedback configuration. In an example, the cardiac blood volume status indicator can be compared to a threshold, and the amount of neuromodulation delivered to the splanchnic region can be adjusted when the cardiac blood volume status indicator is below a first value of the threshold. The cardiac blood volume status indicator can be below of first value of the threshold, for example, in a heart that has been transiently unloaded via neuromodulation, such that the cardiac blood volume has been reduced. Under these conditions, transient loading of the heart can be advantageous, resulting in increased cardiac volume and myocardial stretch. Transient loading of the heart can be performed, for example, by increasing an amount of sympathetic nerve stimulation to the splanchnic region, decreasing an amount of sympathetic nerve inhibition to the splanchnic region, decreasing an amount of parasympathetic nerve stimulation to the splanchnic region, or increasing an amount of parasympathetic nerve inhibition to the splanchnic region. Each of the above examples of neuromodulation can result in splanchnic vasoconstriction, and, in turn, redistribution of blood from the splanchnic region to the heart.

In an example, the cardiac blood volume status indicator can be compared to a threshold, and the amount of neuromodulation delivered to the splanchnic region can be adjusted when the cardiac blood volume status indicator is above a second value of the threshold. The cardiac blood volume status indicator can be above a second value of the threshold, for example, in a heart that has been transiently loaded via neuromodulation, such that the cardiac blood volume has been increased and the myocardium has been stretched. Under these conditions, transient unloading of the heart can be advantageous, resulting in decreased cardiac volume and alleviating myocardial stretch. Transient unloading of the heart can be performed, for example, by decreasing an amount of sympathetic nerve stimulation to the splanchnic region, increasing an amount of sympathetic nerve inhibition to the splanchnic region, increasing an amount of parasympathetic nerve stimulation to the splanchnic region, or decreasing an amount of parasympathetic nerve inhibition to the splanchnic region. Each of the above examples of neuromodulation can result in splanchnic vasodilation, and, in turn, redistribution of blood from the heart to the splanchnic region.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system, comprising:
   a first fluid monitor configured to monitor fluid in a pulmonary region of a patient and provide a pulmonary fluid status;
   a second fluid monitor configured to monitor fluid in a non-pulmonary region of the patient and provide a non-pulmonary fluid status;
   a therapy delivery system configured to vasodilate vasculature in the non-pulmonary region;
   a controller operably connected to the first and second fluid monitors and to the therapy delivery system, the controller configured to determine, using the pulmonary fluid status and the non-pulmonary fluid status, that an elevated fluid status is attributable to fluid distribution toward the pulmonary region rather than to an increase in total blood volume, and to control the therapy delivery system to deliver a therapy to vasodilate vasculature in the non-pulmonary region to redistribute fluid from the pulmonary region to the non-pulmonary region.

2. The system of claim 1, wherein the therapy delivery system is configured to deliver energy to an autonomic neural target.

3. The system of claim 1, wherein the therapy delivery system is configured to deliver spinal cord stimulation to vasodilate vasculature in the non-pulmonary region.

4. The system of claim 1, wherein the therapy delivery system is configured to deliver vagal nerve stimulation target to vasodilate vasculature in the non-pulmonary region.

5. The system of claim 1, wherein the therapy delivery system is configured to deliver neuromodulation to a celiac ganglion.

6. The system of claim 1, wherein the therapy delivery system is configured to deliver neuromodulation to a baroreceptor region.

7. The system of claim 1, wherein the therapy delivery system is configured to deliver neuromodulation to an adrenal nerve.

8. The system of claim 1, wherein the therapy delivery system is configured to deliver a first stimulation to locally vasodilate vasculature in a first location of the non-pulmonary region and deliver a second stimulation to locally vasoconstrict vasculature in a second location of the non-pulmonary region.

9. The system of claim 1, wherein at least one of the first fluid monitor or the second fluid monitor includes an impedance sensor.

10. The system of claim 1, wherein at least one of the first fluid monitor or the second fluid monitor includes an acoustic sensor or a pressure sensor.

11. A method, comprising:
    monitoring fluid in a pulmonary region of a patient to provide a pulmonary fluid status;
    monitoring fluid in a non-pulmonary region of the patient to provide a non-pulmonary fluid status, wherein monitoring fluid in the non-pulmonary region includes monitoring fluid in at least one of a splanchnic region or a leg region of the patient;
    determining, using the pulmonary fluid status and the non-pulmonary fluid status, that an elevated pulmonary fluid status is attributable to fluid distribution toward the pulmonary region rather than to an increase in total blood volume;
    delivering a therapy to vasodilate vasculature in the non-pulmonary region to redistribute fluid from the pulmonary region to the non-pulmonary region.

12. The method of claim 11, wherein delivering the therapy to vasodilate vasculature in the non-pulmonary region includes delivering energy to an autonomic neural target to vasodilate vasculature in the non-pulmonary region.

13. The method of claim 11, wherein delivering therapy to vasodilate vasculature in the non-pulmonary region includes delivering spinal cord stimulation to vasodilate vasculature in the non-pulmonary region.

14. The method of claim 11, wherein delivering therapy to vasodilate vascular beds in the non-pulmonary region includes vagal nerve stimulation target to vasodilate vasculature in the non-pulmonary region.

15. The method of claim 11, wherein delivering therapy to vasodilate vascular beds in the non-pulmonary region includes delivering neuromodulation to a celiac ganglion.

16. The method of claim 11, wherein delivering therapy to vasodilate vascular beds in the non-pulmonary region includes delivering baroreceptor stimulation.

17. The method of claim 11, wherein delivering therapy to vasodilate vascular beds in the non-pulmonary region includes delivering neuromodulation to an adrenal nerve.

18. The method of claim 11, wherein delivering a therapy to vasodilate vasculature in the non-pulmonary region includes delivering a first stimulation to locally vasodilate vasculature in a first location of the non-pulmonary region and delivering a second stimulation to locally vasoconstrict vasculature in a second location of the non-pulmonary region.

19. The method of claim 11, wherein at least one of monitoring fluid in the pulmonary region or monitoring fluid in the non-pulmonary region includes monitoring fluid using sensed impedance.

20. The method of claim 11, wherein at least one of monitoring fluid in the pulmonary region or monitoring fluid in the non-pulmonary region includes monitoring fluid using an acoustic sensor or a pressure sensor.

\* \* \* \* \*